US007727229B2

(12) United States Patent
He et al.

(10) Patent No.: US 7,727,229 B2
(45) Date of Patent: *Jun. 1, 2010

(54) METHOD AND APPARATUS FOR ALTERING CONDUCTION PROPERTIES IN THE HEART AND IN ADJACENT VESSELS

(75) Inventors: Ding Sheng He, Tyngsboro, MA (US); David MacAdam, Millbury, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 1297 days.

This patent is subject to a terminal disclaimer.

(21) Appl. No.: 10/475,915

(22) PCT Filed: Mar. 15, 2002

(86) PCT No.: PCT/US02/07671

§ 371 (c)(1), (2), (4) Date: May 10, 2004

(87) PCT Pub. No.: WO02/087456

PCT Pub. Date: Nov. 7, 2002

(65) Prior Publication Data

US 2005/0119647 A1 Jun. 2, 2005

Related U.S. Application Data

(60) Provisional application No. 60/287,768, filed on May 1, 2001.

(51) Int. Cl.
*A61B 18/18* (2006.01)
*A61B 5/04* (2006.01)
(52) U.S. Cl. .................... 606/41; 600/374; 607/122
(58) Field of Classification Search .............. 606/41, 606/48–50; 600/374; 607/122
See application file for complete search history.

(56) References Cited

U.S. PATENT DOCUMENTS

| 3,996,938 A | 12/1976 | Clark, III |
| 4,660,571 A | 4/1987 | Hess et al. |
| 4,664,120 A | 5/1987 | Hess |

(Continued)

FOREIGN PATENT DOCUMENTS

EP  0 428 279  4/1991

(Continued)

OTHER PUBLICATIONS

Chauvin et al., "The Anatomic Basis of Connections Between the Coronary Sinus Musculature and the Left Atrium in Humans," Circulation 2000; 101; 647-652.

(Continued)

*Primary Examiner*—Michael Peffley
(74) *Attorney, Agent, or Firm*—Wolf, Greenfield & Sacks, P.C.

(57) ABSTRACT

Method and apparatus for treating conductive irregularities in the heart, particularly atrial fibrillation and accessory path arrythmias. An ablative catheter is positioned relative to an inter-atrial electrical pathway, or a vicinity of accessory paths such as the coronary sinus or fossa ovalis, and actuated to form a lesion that partially or completely blocks electrical conduction in at least one direction along the pathway.

29 Claims, 31 Drawing Sheets

U.S. PATENT DOCUMENTS

| | | | |
|---|---|---|---|
| 4,699,147 A | | 10/1987 | Chilson et al. |
| 4,709,698 A | | 12/1987 | Johnston et al. |
| 4,921,404 A | | 5/1990 | Holmberg |
| 4,921,484 A | | 5/1990 | Hillstead |
| 4,940,064 A | | 7/1990 | Desai |
| 5,010,894 A | | 4/1991 | Edhag |
| 5,100,423 A | | 3/1992 | Fearnot |
| 5,190,542 A | | 3/1993 | Nakao et al. |
| 5,215,103 A | | 6/1993 | Desai |
| 5,231,995 A | | 8/1993 | Desai |
| 5,255,679 A | | 10/1993 | Imran |
| 5,311,866 A | * | 5/1994 | Kagan et al. ............... 600/374 |
| 5,313,943 A | | 5/1994 | Houser et al. |
| 5,324,284 A | | 6/1994 | Imran |
| 5,365,926 A | | 11/1994 | Desai |
| 5,383,852 A | | 1/1995 | Stevens-Wright et al. |
| 5,385,146 A | * | 1/1995 | Goldreyer ................. 600/374 |
| 5,397,339 A | | 3/1995 | Desai |
| 5,397,341 A | | 3/1995 | Hirschberg et al. |
| 5,400,783 A | | 3/1995 | Pomeranz et al. |
| 5,403,311 A | | 4/1995 | Abele et al. |
| 5,409,000 A | | 4/1995 | Imran |
| 5,411,025 A | * | 5/1995 | Webster, Jr. ............... 600/374 |
| 5,415,166 A | | 5/1995 | Imran |
| 5,433,198 A | | 7/1995 | Desai |
| 5,465,717 A | | 11/1995 | Imran et al. |
| 5,476,495 A | * | 12/1995 | Kordis et al. ............... 607/122 |
| 5,549,108 A | | 8/1996 | Edwards et al. |
| 5,575,810 A | | 11/1996 | Swanson et al. |
| 5,611,777 A | | 3/1997 | Bowden et al. |
| 5,617,854 A | * | 4/1997 | Munsif ...................... 600/374 |
| 5,636,634 A | | 6/1997 | Kordis et al. |
| 5,653,684 A | | 8/1997 | Laptewicz et al. |
| 5,680,860 A | | 10/1997 | Imran |
| 5,681,280 A | | 10/1997 | Rusk et al. |
| 5,702,438 A | | 12/1997 | Avitall |
| 5,722,403 A | | 3/1998 | McGee et al. |
| 5,800,482 A | | 9/1998 | Pomeranz et al. |
| 5,813,997 A | | 9/1998 | Imran et al. |
| 5,836,947 A | | 11/1998 | Fleischman et al. |
| 5,860,974 A | | 1/1999 | Abele |
| 5,868,706 A | | 2/1999 | Cox |
| 5,891,136 A | | 4/1999 | McGee et al. |
| 5,893,885 A | | 4/1999 | Webster, Jr. |
| 5,904,698 A | | 5/1999 | Thomas et al. |
| 5,913,854 A | * | 6/1999 | Maguire et al. ............... 606/41 |
| 5,916,213 A | | 6/1999 | Haissaguerre et al. |
| 5,921,982 A | | 7/1999 | Lesh et al. |
| 5,928,260 A | | 7/1999 | Chin et al. |
| 5,931,863 A | | 8/1999 | Griffin, III et al. |
| 5,951,471 A | | 9/1999 | de la Rama et al. |
| 5,968,040 A | | 10/1999 | Swanson et al. |
| 6,001,093 A | | 12/1999 | Swanson et al. |
| 6,029,671 A | | 2/2000 | Stevens et al. |
| 6,052,607 A | | 4/2000 | Edwards et al. |
| 6,071,282 A | | 6/2000 | Fleischman |
| 6,146,379 A | | 11/2000 | Fleischman et al. |
| 6,240,307 B1 | * | 5/2001 | Beatty et al. ............... 600/374 |
| 6,315,778 B1 | * | 11/2001 | Gambale et al. ............... 606/41 |
| 6,375,668 B1 | | 4/2002 | Gifford et al. |
| 6,500,174 B1 | | 12/2002 | Maguire et al. |
| 6,616,655 B1 | * | 9/2003 | Falwell et al. ............... 606/41 |
| 6,837,886 B2 | * | 1/2005 | Collins et al. ............... 606/41 |
| 6,917,834 B2 | | 7/2005 | Koblish et al. |
| 7,255,695 B2 | * | 8/2007 | Falwell et al. ............... 606/41 |
| 7,306,594 B2 | * | 12/2007 | Collins et al. ............... 606/41 |
| 2001/0007070 A1 | | 7/2001 | Stewart et al. |
| 2005/0119647 A1 | * | 6/2005 | He et al. .................. 606/41 |
| 2005/0256521 A1 | * | 11/2005 | Kozel .................... 606/41 |
| 2007/0129717 A1 | * | 6/2007 | Brown et al. ............... 606/41 |

FOREIGN PATENT DOCUMENTS

| | | |
|---|---|---|
| EP | 0 771 547 | 6/1997 |
| EP | 0 790 066 | 8/1997 |
| EP | 0 982 047 | 3/2000 |
| GB | 2271932 | 4/1994 |
| WO | WO 93/16632 | 9/1993 |
| WO | WO 94/00178 | 1/1994 |
| WO | WO 94/06349 | 3/1994 |
| WO | WO 94/16618 | 8/1994 |
| WO | WO 94/21165 | 9/1994 |
| WO | WO 94/21167 | 9/1994 |
| WO | WO 94/21168 | 9/1994 |
| WO | WO 95/01751 | 1/1995 |
| WO | WO 95/10319 | 4/1995 |
| WO | WO 97/17892 | 5/1997 |
| WO | WO 99/15225 | 4/1999 |
| WO | WO 99/56812 | 11/1999 |
| WO | WO 99/62413 | 12/1999 |
| WO | WO 00/67656 | 11/2000 |
| WO | WO 00/72909 | 12/2000 |
| WO | WO 00/74555 | 12/2000 |
| WO | WO 01/17451 | 3/2001 |
| WO | WO 01/82814 | 12/2001 |
| WO | WO 02/087456 | 11/2002 |

OTHER PUBLICATIONS

Olgin et al., "Ablation of Atrial Fibrillation," Nov. 1997, J. Cardiovascular Electrophysiology, v. 8, p. 1266-1268.

* cited by examiner

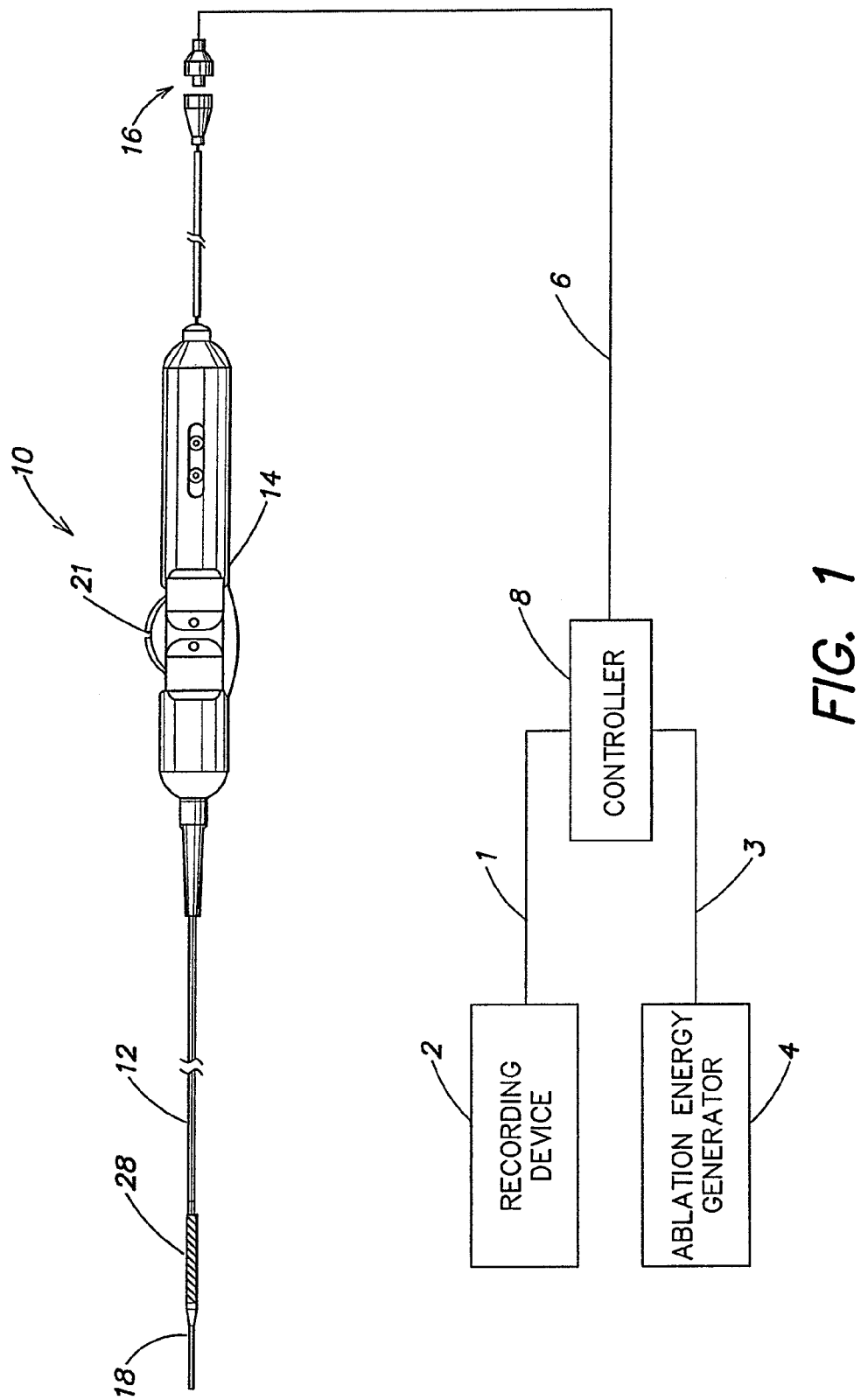

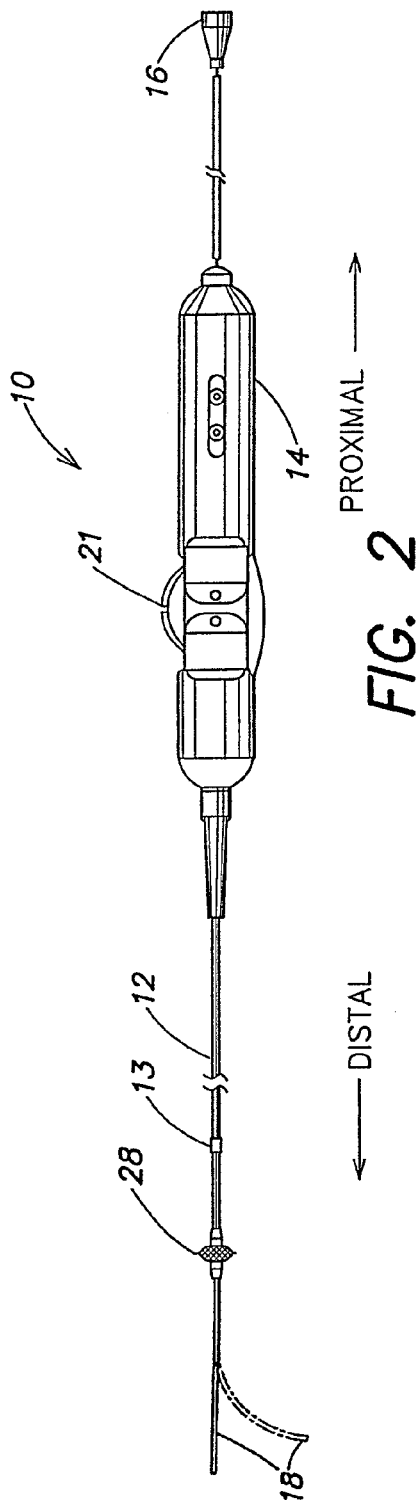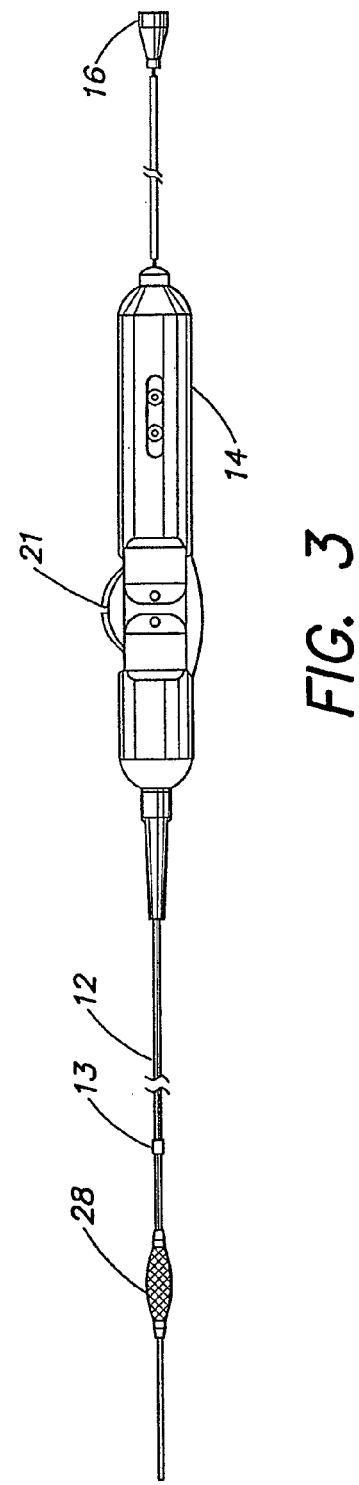

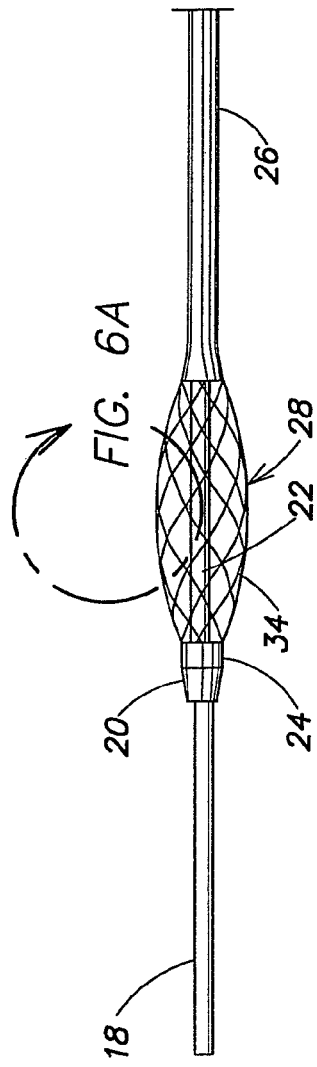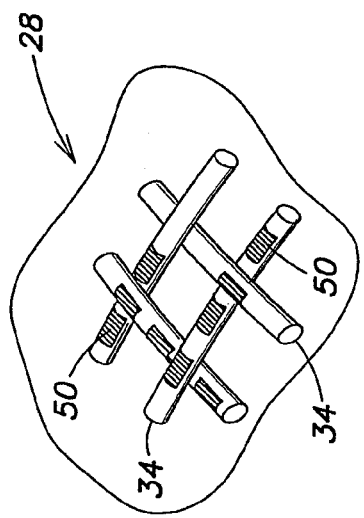

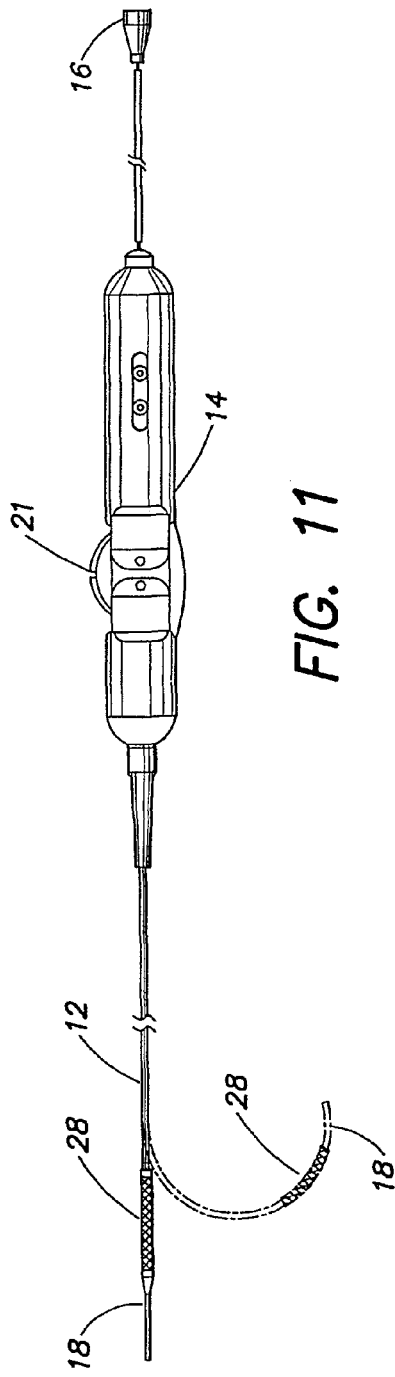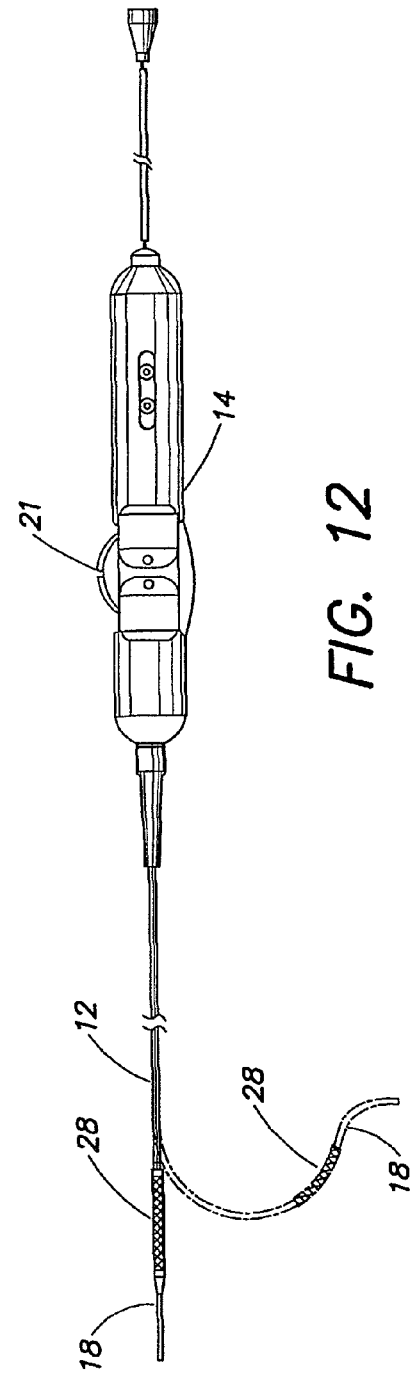
FIG. 11
FIG. 12

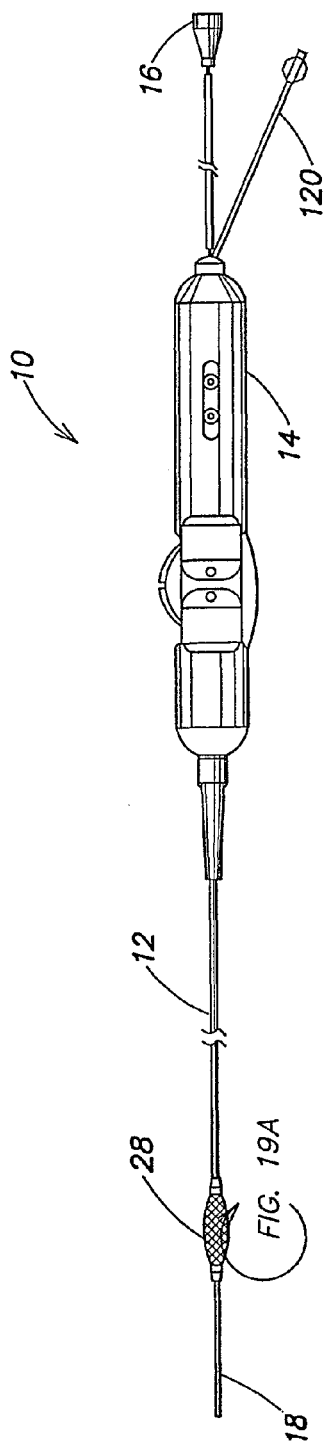
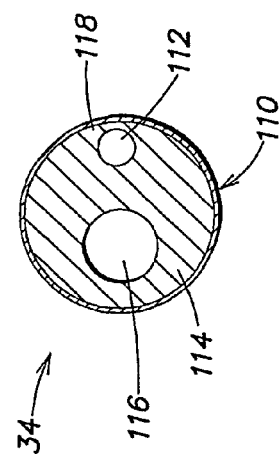
FIG. 19
FIG. 19A

METHOD AND APPARATUS FOR ALTERING CONDUCTION PROPERTIES IN THE HEART AND IN ADJACENT VESSELS

CROSS REFERENCE TO RELATED APPLICATION

This application claims the benefit of U.S. provisional application Ser. No. 60/287,768 entitled "Catheterization Method of Altering Conduction Properties Along Pathways in the Heart and in Vessels in Conductive Communications with the Heart," filed May 1, 2001, which is incorporated herein by reference.

FIELD OF THE INVENTION

The invention relates to one or more catheterization methods of altering conduction properties along pathways in the heart, and in vessels in conductive communication with the heart, and is particularly related to methods of ablative catheter treatment of atrial fibrillation and arrhythmias of accessory pathways.

BACKGROUND OF THE INVENTION

The human heart is a very complex organ, which relies on both muscle contraction and electrical impulses to function properly. Electrical impulses travel through the heart in a desired sequence so that the various chambers receive and pump blood in the proper order. With respect to the atria, normal excitation is propagated in a right atrium to left atrium direction via inter-atrial conduction pathways, including the coronary sinus, fossa ovalis, and Bachmann's bundle.

Abnormal inter-atrial electric flow, such as left-to-right conduction, may pose serious health risks to a patient including atrial fibrillation. Catheter ablation, that is the application of energy at a distal portion of a catheter positioned within or about the heart, or a vessel in electrical communication with the heart, to form lesions that alter conductive properties in the heart, is known for treating atrial fibrillation. Such techniques have targeted the focal trigger of an atrial arrhythmia as well as reentrant circuits in the myocardium.

SUMMARY OF THE INVENTION

One illustrative embodiment of the invention is directed to a method of treating atrial fibrillation. The method comprises providing a catheter including a distal portion having an arrangement for conductive alteration of an inter-atrial conductive pathway of the heart, positioning the distal portion of the catheter relative to a portion of the inter-atrial conductive pathway, and actuating the conductive alteration arrangement to alter the conduction of the inter-atrial conductive pathway.

Another illustrative embodiment of the invention is directed to a method for treating arrhythmia of an accessory pathway of the heart. The method comprises providing a catheter including a distal portion having an arrangement for conductive alteration of a portion of the heart and/or of a vessel in communication with the heart that is in the vicinity of an accessory pathway, positioning the distal portion of the catheter relative to the portion of the heart and/or of the vessel in the vicinity of the accessory pathway, and actuating the conductive alteration arrangement to alter the conduction of the accessory pathway.

A further illustrative embodiment of the invention is directed to a method for treating a condition of the heart. The method comprises acts of introducing a catheter into the heart, the catheter having a braided conductive member at a distal end thereof, forming a lesion on tissue at a selected location of the heart with the braided conductive member, and measuring the quality of the lesion with the braided conductive member.

Another illustrative embodiment of the invention is directed to a catheter having a braided conductive member. The braided conductive member comprises one or more ablation filaments for applying ablative energy to a surface of a heart, and one or more mapping filaments for measuring an electrical signal at a surface of the heart.

A further illustrative embodiment of the invention is directed to a method for treating a condition of a heart. The method comprises an act of using a catheter having a braided conductive member to create a lesion at a location selected from the group consisting of a wall of the coronary sinus, a wall of the right atrium at the opening of the coronary sinus, a wall of the right atrium at the fossa ovalis, and a wall of the left atrium at the fossa ovalis.

Another illustrative embodiment of the invention is directed to a method for treating cardiac arrhythmia. The method comprises acts of introducing a catheter into the right atrium of a patient, the catheter having a braided conductive member at a distal end thereof, passing the braided conductive member of the catheter through the inter-atrial septum separating the right atrium and the left atrium, expanding the braided conductive member in the left atrium of the patient, positioning the braided conductive member so that the braided conductive member contacts the inter-atrial septum, and applying energy to the inter-atrial septum via the braided conductive member to create a lesion on the inter-atrial septum.

A further illustrative embodiment of the invention is directed to a method for treating cardiac arrhythmia. The method comprises acts of introducing a catheter into the right atrium of a patient, the catheter having a braided conductive member at a distal end thereof, passing the distal end of the catheter through the inter-atrial septum separating the right atrium and the left atrium, expanding the braided conductive member in the right atrium of the patient, positioning the braided conductive member so that the braided conductive member contacts the inter-atrial septum, and applying energy to the inter-atrial septum via the braided conductive member to create a lesion on the inter-atrial septum.

Another illustrative embodiment of the invention is directed to a method for treating atrial fibrillation in a heart. The method comprises an act of using a catheter having a braided conductive member to ablate a region of the heart that serves as an electrical pathway between that left atrium and the right atrium of the heart to alter the conductivity of the electrical pathway.

A further illustrative embodiment of the invention is directed to a method for treating a condition of the heart. The method comprises acts of introducing a catheter into the heart, the catheter having a braided conductive member, forming a lesion in the heart with the braided conductive member, generating a pacing signal at a pacing electrode on the catheter on a first side of the braided conductive member, and detecting a received signal at a detection electrode on the catheter on a second side of the braided conductive member, wherein the received signal is related to a quality of the lesion.

The features and advantages of the present invention will be more readily understood and apparent from the following detailed description of the invention, which should be read in conjunction with the accompanying drawings, and from the claims which are appended at the end of the Detailed Description.

BRIEF DESCRIPTION OF THE DRAWINGS

In the drawings, which are incorporated herein by reference and in which like elements have been given like references characters, FIG. 1 illustrates an overview of a mapping and ablation catheter system;

FIGS. 2 and 3 illustrate further details of the catheter illustrated in FIG. 1;

FIGS. 4-7 illustrate further details of the braided conductive member illustrated in FIGS. 2 and 3;

FIGS. 11-13 illustrate further details of the steering capabilities of the catheter;

FIGS. 18-19 illustrate the use of irrigation in connection with the catheter;

DETAILED DESCRIPTION

Figure 4:
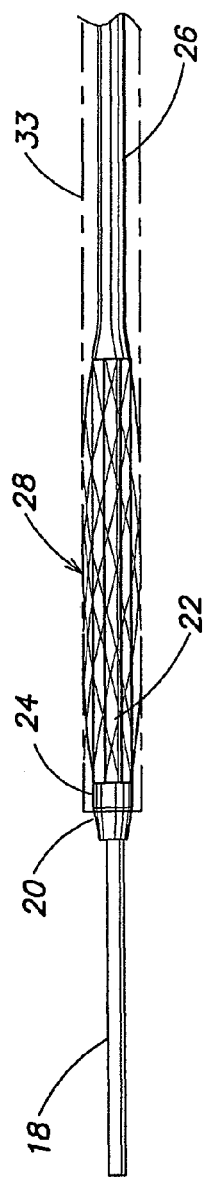

One embodiment of the present invention is a catheterization method for altering the conductive properties of electrically conductive pathways in the heart and in vessels in electrical communication with the heart. The catheterization method is particularly suited for treating atrial fibrillation and arrhythmias of accessory pathways, e.g., the coronary sinus or fossa ovalis. In connection with treating atrial fibrillation, the catheterization method includes the step of altering electrical flow along one or more of the preferential inter-atrial conduction paths: coronary sinus ("CS"), Bachmann's bundle and the fossa ovalis. In connection with treating arrythmias of accessory pathways, the conductive properties of the coronary sinus may be altered. Conductive alteration of the coronary sinus may encompass altering the conductivity of the wall of the coronary sinus, the ostium of the coronary sinus, or the musculature surrounding the coronary sinus. Further, in connection with treating arrythmias of accessory pathways, the conductive properties of the fossa ovalis may be altered. Conductive alteration of the fossa ovalis may encompass altering the conductivity of the fossa ovalis or the inter-atrial tissue around the fossa ovalis. Conductive alteration in connection with the inventive catheterization method does not necessarily mean the formation of a complete conduction block. Rather, a complete block, a partial block, or any therapeutically effective change in conductive properties is within the meaning of conductive alteration for purposes of this patent.

An ablative catheter is a preferred device for altering conductive properties in and around the heart. The ablative catheter is employed to create one or more lesions that may alter electrical flow along a targeted pathway in the heart and/or in a vessel in conductive communication with the heart. Energy may be employed to scarify the atrial conduction path or accessory path and may be generated by any of a variety of sources including RF, DC, ultrasound, microwave, laser, or cryothermal. Non-electrical approaches to forming a lesion to disturb undesired left-to-right atrial impulses also are contemplated as should be apparent to one of skill in the art. One or more lesions or other conduction alternative structure may be applied at a location, in the interior or the exterior of the heart or a blood vessel that is in conductive communication with the heart. The lesion or lesions may extend circumferentially about or within a target blood vessel. For example, in connection with ablation of the coronary sinus, an annular lesion may be formed at or near the ostium. The circumferential lesion need not be continuous; that is, scarred or necrotic segments may be spaced in a circumferential fashion even though one or more of the segments is not contiguous with an adjacent segment. Other lesion arrangements also are contemplated so long as the lesion leads to a reduction in undesired conduction. As observed above, although lesion formation by application of electrical energy is preferred, other arrangements for producing lesions are contemplated as are other forms of conduction alteration structures.

The location of the undesired conduction path in the heart or adjoining vessels may be determined by any suitable manner, including endocardial mapping. Mapping typically involves percutaneously introducing a catheter having one or more electrodes into the patient, passing the catheter through a blood vessel (e.g. the femoral vein or artery) and into an endocardial site (e.g., the atrium of the heart), and deliberately inducing an arrhythmia so that a continuous, simultaneous recording can be made with a multichannel recorder at each of several different endocardial positions. When the errant conduction path is located, as indicated in the electrocardiogram recording, it is marked by various imaging or localization means. An ablation catheter with one or more electrodes can then transmit electrical energy to the tissue adjacent the electrode to create a lesion in the tissue. One or more suitably positioned lesions will typically create a region of necrotic tissue which serves to disable the propagation of the aberrant impulse. Ablation is carried out by applying energy to the catheter electrodes. The ablation energy can be, for example, RF, DC, ultrasound, microwave, cryogenic or laser radiation. The same catheter may be used both for mapping and ablation, or two or more different catheters may be employed.

Conventional atrial ablation catheters may be employed to create the desired disturbance of an inter-atrial conduction pathway, including single point electrode catheters, balloon electrode catheters, and loop electrode catheters. The inventors have found that a catheter including a braided conductive member, such as a wire mesh, is particularly suited for treatment of inter-atrial fibrillation by ablation of one or more of the inter-atrial conduction paths and also is indicated for treatment of accessory path arrythmias by the ablation of the vicinity of the coronary sinus ostium. The mesh may have a slender configuration compatible with percutaneous transport and an expanded deployed configuration suitable for contacting the region of undesired conduction and, when energized, will apply a suitable lesion to block propagation of the undesired electrical signals such as between the left and right atria in connection with the treatment of atrial fibrillation.

System Overview

Reference is now made to FIG. 1, which figure illustrates an overview of a mapping and ablation catheter system in accordance with the present invention. The system includes a catheter 10 having a shaft portion 12, a control handle 14, and a connector portion 16. A controller 8 is connected to connector portion 16 via cable 6. Ablation energy generator 4 may be connected to controller 8 via cable 3. A recording device 2 may be connected to controller 8 via cable 1. When used in an ablation application, controller 8 is used to control ablation energy provided by ablation energy generator 4 to catheter 10. When used in a mapping application, controller 8 is used to process signals coming from catheter 10 and to provide these signals to recording device 2. Although illustrated as separate devices, recording device 2, ablation energy generator 4, and controller 8 could be incorporated into a single device. In one embodiment, controller 8 may be a QUADRAPULSE RF CONTROLLER™ device available from CR Bard, Inc., Murray Hill, N.J.

In this description, various aspects and features of the present invention will be described. The various features of the invention are discussed separately for clarity. One skilled in the art will appreciate that the features may be selectively combined in a device depending upon the particular application. Furthermore, any of the various features may be incorporated in a catheter and associated method of use for either mapping or ablation procedures.

Catheter Overview

Reference is now made to FIGS. 2-7, which figures illustrate one embodiment of the present invention. The present invention generally includes a catheter and method of its use for mapping and ablation in electrophysiology procedures. Catheter 10 includes a shaft portion 12, a control handle 14, and a connector portion 16. When used in mapping applications, connector portion 16 is used to allow signal wires running from the electrodes at the distal portion of the catheter to be connected to a device for processing the electrical signals, such as a recording device.

Catheter 10 may be a steerable device. FIG. 2 illustrates the distal tip portion 18 being deflected by the mechanism contained within control handle 14. Control handle 14 may include a rotatable thumb wheel which can be used by a user to deflect the distal end of the catheter. The thumb wheel (or any other suitable actuating device) is connected to one or more pull wires which extend through shaft portion 12 and are connected to the distal end 18 of the catheter at an off-axis location, whereby tension applied to one or more of the pull wires causes the distal portion of the catheter to curve in a predetermined direction or directions. U.S. Pat. Nos. 5,383,852, 5,462,527, and 5,611,777, which are hereby incorporated by reference, illustrate various embodiments of control handle 14 that may be used for steering catheter 10.

Shaft portion 12 includes a distal tip portion 18, a first stop 20 and an inner member 22 connected to the first stop portion 20. Inner member 22 may be a tubular member. Concentrically disposed about inner member 22 is a first sheath 24 and a second sheath 26. Also concentrically disposed about inner member 22 is a braided conductive member 28 anchored at respective ends 30 and 32 to the first sheath 24 and the second sheath 26, respectively.

Figure 5:
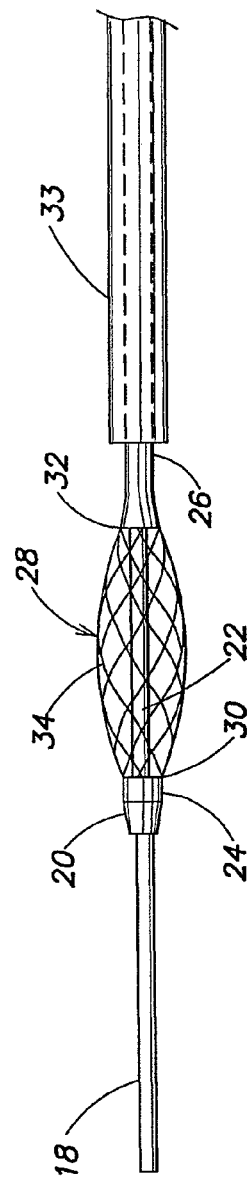

In operation, advancing the second sheath 26 distally over inner member 22 causes the first sheath 24 to contact stop 20. Further distal advancement of the second sheath 26 over inner member 22 causes the braided conductive member 28 to expand radially to assume various diameters and/or a conical shape. FIGS. 1 and 4 illustrate braided conductive member 28 in an unexpanded (collapsed or "undeployed") configuration. FIGS. 3, 5, and 6 illustrate braided conductive member 28 in a partially expanded condition. FIG. 2 illustrates braided conductive member 28 radially expanded ("deployed") to form a disk. Further movement of inner member 22, first sheath 24, and second sheath 26 with respect to each other may be used to form the conical shape previously referred to and in particular the braided conductive member may be formed into a cone having a distal-facing tissue contacting and/or a cone having a proximal-facing tissue contact ring.

Alternatively, braided conductive member 28 can be radially expanded by moving inner member 22 proximally with respect to the second sheath 26.

As another alternative, inner member 22 and distal tip portion 18 may be the same shaft and stop 20 may be removed. In this configuration, sheath 24 moves over the shaft in response to, for example, a mandrel inside shaft 22 and attached to sheath 24 in the manner described, for example, in U.S. Pat. No. 6,178,354, which is incorporated herein by reference.

As illustrated particularly in FIGS. 4 and 5 a third sheath 33 may be provided. The third sheath serves to protect shaft portion 12 and in particular braided conductive member 28 during manipulation through the patient's vasculature. In addition, the third sheath 33 shields braided conductive member 28 from the patient's tissue in the event ablation energy is prematurely delivered to the braided conductive member 28.

The respective sheaths 24, 26, and 33 can be advanced and retracted over the inner member 22, which may be a tubular member, in many different manners. Control handle 14 may be used. U.S. Pat. Nos. 5,383,852, 5,462,527, and 5,611,777 illustrate examples of control handles that can control sheaths 24, 26, and 33. As described in these incorporated by reference patents, control handle 14 may include a slide actuator which is axially displaceable relative to the handle. The slide actuator may be connected to one of the sheaths, for example, the second sheath 26 to control the movement of the sheath 26 relative to inner member 22, to drive braided conductive member 28 between respective collapsed and deployed positions, as previously described. Control handle 14 may also include a second slide actuator or other mechanism coupled to the retractable outer sheath 32 to selectively retract the sheath in a proximal direction with respect to the inner member 22.

Braided conductive member 28 is, in one embodiment of the invention, a plurality of interlaced, electrically conductive filaments 34. Braided conductive member 28 may be a wire mesh. The filaments are flexible and capable of being expanded radially outwardly from inner member 22. The filaments 34 are preferably formed of metallic elements having relatively small cross sectional diameters, such that the filaments can be expanded radially outwardly. The filaments may be round, having a dimension on the order of about 0.001-0.030 inches in diameter. Alternatively, the filaments may be flat, having a thickness on the order of about 0.001-0.030 inches, and a width on the order of about 0.001-0.030 inches. The filaments may be formed of Nitinol type wire. Alternatively, the filaments may include non metallic elements woven with metallic elements, with the non metallic elements providing support to or separation of the metallic elements. A multiplicity of individual filaments 34 may be provided in braided conductive member 28, for example up to 300 or more filaments.

Each of the filaments 34 can be electrically isolated from each other by an insulation coating. This insulation coating may be, for example, a polyamide type material. A portion of the insulation on the outer circumferential surface 60 of braided conductive member 28 is removed. This allows each of the filaments 34 to form an isolated electrode, not an electrical contact with any other filament, that may be used for mapping and ablation. Alternatively, specific filaments may be permitted to contact each other to form a preselected grouping.

Each of the filaments 34 is helically wound under compression about inner member 22. As a result of this helical construction, upon radial expansion of braided conductive member 28, the portions of filaments 34 that have had the insulation stripped away do not contact adjacent filaments and thus, each filament 34 remains electrically isolated from every other filament. FIGS. 6 and 6A illustrate how the insulation may be removed from individual filaments 34 while still providing isolation between and among the filaments. As illustrated in FIG. 6A, regions 50 illustrate regions, on the outer circumferential surface 60 of braided conductive member 28, where the insulation has been removed from individual filaments 34. In one embodiment of the invention, the insulation may be removed from up to one half of the outer facing circumference of each of the individual filaments 34 while still retaining electrical isolation between each of the filaments 34.

The insulation on each of the filaments 34 that comprise braided conductive member 28 may be removed about the outer circumferential surface 60 of braided conductive member 28 in various ways. For example, one or more circumferential bands may be created along the length of braided conductive member 28. Alternatively, individual sectors or quadrants only may have their insulation removed about the circumference of braided conductive member 28. Alternatively, only selected filaments 34 within braided conductive member 28 may have their circumferentially facing insulation removed. Thus, an almost limitless number of configurations of insulation removal about the outer circumferential surface 60 of braided conductive member 28 can be provided depending upon the mapping and ablation characteristics and techniques that a clinician desires.

The insulation on each of the filaments 34 may be removed at the outer circumferential surface 60 of braided conductive member 28 in a variety of ways as long as the insulation is maintained between filaments 34 so that filaments 34 remain electrically isolated from each other.

The insulation can be removed from the filaments 34 in a variety of ways to create the stripped portions 50 on braided conductive member 28. For example, mechanical means such as abration or scraping may be used. In addition, a water jet, chemical means, or thermal radiation means may be used to remove the insulation.

In one example of insulation removal, braided conductive member 28 may be rotated about inner member 22, and a thermal radiation source such as a laser may be used to direct radiation at a particular point along the length of braided conductive member 28. As the braided conductive member 28 is rotated and the thermal radiation source generates heat, the insulation is burned off the particular region.

Insulation removal may also be accomplished by masking selected portions of braided conductive member 28. A mask, such as a metal tube may be placed over braided conducive member 28. Alternatively, braided conductive member 28 may be wrapped in foil or covered with some type of photoresist. The mask is then removed in the areas in which insulation removal is desired by, for example, cutting away the mask, slicing the foil, or removing the photoresist. Alternatively, a mask can be provided that has a predetermined insulation removal pattern. For example, a metal tube having cutouts that, when the metal tube is placed over braided conductive member 28, exposes areas where insulation is to be removed.

Figure 7:
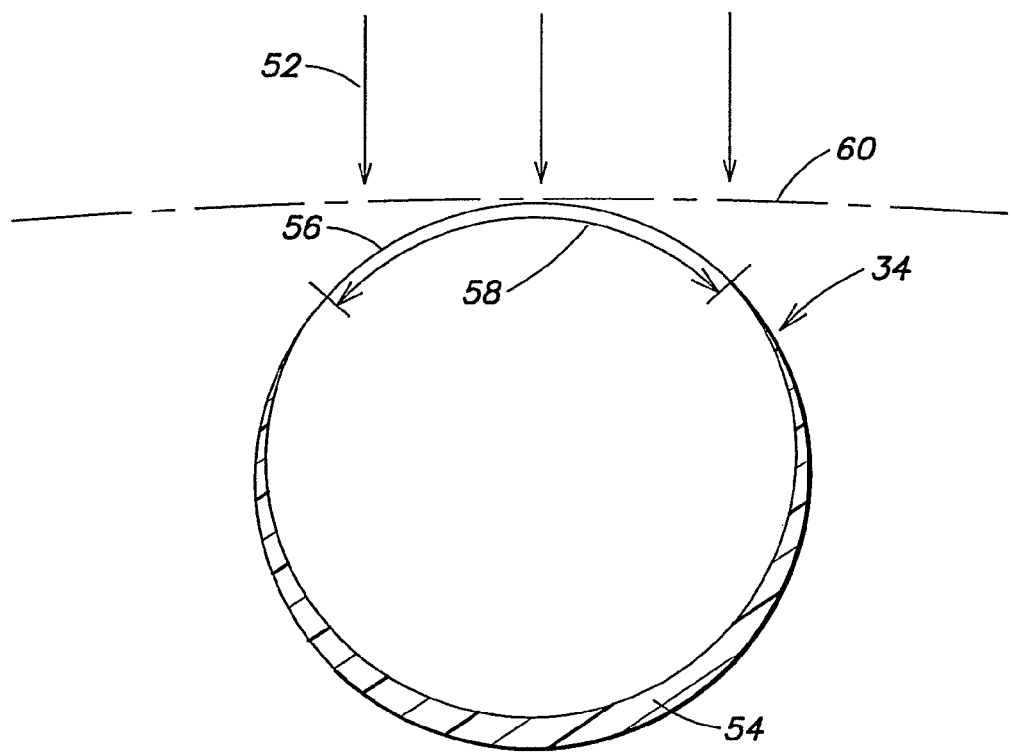

FIG. 7 illustrates how thermal radiation 52 may be applied to the outer circumferential surface 56 of a respective filament 34 that defines the outer circumferential surface 60 of braided conductive member 28. As thermal radiation 52 is applied, the insulation 54 is burned off or removed from the outer circumference 56 of wire 34 to create a region 58 about the circumference 56 of filament 34 that has no insulation.

The insulation 54 can also be removed in a preferential manner so that a particular portion of the circumferential surface 56 of a filament 34 is exposed. Thus, when braided conductive. member 28 is radially expanded, the stripped portions of filaments may preferentially face the intended direction of mapping or ablation.

Although removal of insulation from filaments 34 in the vicinity of the outer circumferential surface 60 has been discussed in detail above, insulation can be removed from one or more filaments 34 that comprise braided conductive member 28 anywhere along the length of the filament. For example, as illustrated in U.S. Pat. No. 6,315,778, which is incorporated herein by reference, braided conductive member 28 may be expanded so that it forms a distal-facing ring. In this configuration, the insulation may be removed from filaments 34 in the vicinity of the distal-facing ring. In another embodiment, braided conductive member 28 may be expanded so that it forms a proximal-facing ring and insulation may be removed in the vicinity of the proximal-facing ring. Insulation may be selectively removed to define mapping and/or ablation filaments anywhere on the proximal side, distal side, or circumferential surface of braided conductive member 28 when in its expanded or deployed configuration.

With the insulation removed from the portions of filaments 34 on the outer circumferential surface 60 of braided conductive member 28, a plurality of individual mapping and ablation channels can be created. A wire runs from each of the filaments 34 within catheter shaft 12 and control handle 14 to connector portion 16. A multiplexer or switch box may be connected to the conductors so that each filament 34 may be controlled individually. This function may be incorporated into controller 8. A number of filaments 34 may be grouped together for mapping and ablation. Alternatively, each individual filament 34 can be used as a separate mapping channel for mapping individual electrical activity within a blood vessel at a single point. Using a switch box or multiplexer to configure the signals being received by filaments 34 or ablation energy sent to filaments 34 results in an infinite number of possible combinations of filaments for detecting electrical activity during mapping procedures and for applying energy during an ablation procedure.

The ability to individually define a filament 34 as a mapping or ablation channel may be combined with selective insulation removal from a filament to create a wide variety of mapping/ablation configurations. For example, insulation may be removed from a number of filaments to create an ablative ring around the outer circumferential surface of braided conductive member 28 and insulation may be selectively removed from another filament on the proximal and/or distal side of a filament that is inside the ablative ring but electrically insulated from the filaments forming the ablative ring to define a mapping channel. This can allow a user to ablate tissue in contact with the ring and then check for electrical activity inside the ring using the filament defined as the mapping channel before, during, and/or after an ablation operation. In another embodiment, the ablative ring can be formed inside a mapping channel to allow checking electrical activity outside the ablative ring. These configurations can also be combined to provide an outer mapping channel or channels outside the ablative ring, an ablation ring (or element), and an inner mapping channel or channels inside the ablation ring or element concentrically arranged about the catheter shaft.

In accordance with the invention, a single catheter that provides both mapping and ablation functions can reduce the number of catheter changes needed during an electrophysiology procedure and can allow feedback simultaneously with or shortly after ablation to determine the effectiveness of an ablation operation.

By controlling the amount of insulation that is removed from the filaments 34 that comprise braided conductive member 28, the surface area of the braid that is in contact with a blood vessel wall can also be controlled. This in turn will allow control of the impedance presented to an ablation energy generator, for example, generator 4. In addition, selectively removing the insulation can provide a predetermined or controllable profile of the ablation energy delivered to the tissue.

The above description illustrates how insulation may be removed from the filaments 34. Alternatively, the same features and advantages can be achieved by adding insulation to filaments 34. For example, filaments 34 may be bare wire and insulation can be added to them.

Individual control of the electrical signals received from filaments 34 allows catheter 10 to be used for bipolar (differential or between filament) type mapping as well as unipolar (one filament with respect to a reference) type mapping.

Catheter 10 may also have, as illustrated in FIGS. 2 and 3, a reference electrode 13 mounted on shaft 12 so that reference electrode 13 is located outside the heart during unipolar mapping operations.

Radiopaque markers can also be provided for use in electrode orientation and identification.

One skilled in the art will appreciate all of the insulation can be removed from filaments 34 to create a large ablation electrode.

Although a complete catheter steerable structure has been illustrated, the invention can also be adapted so that inner tubular member 22 is a catheter shaft, guide wire, or a hollow tubular structure for introduction of saline, contrast media, heparin or other medicines, or introduction of guidewires, or the like.

Temperature Sensing

A temperature sensor or sensors, such as, but not limited to, one or more thermocouples may be attached to braided conductive member 28 for temperature sensing during ablation procedures. A plurality of thermocouples may also be woven into the braided conductive member 28. An individual temperature sensor could be provided for each of the filaments 34 that comprise braided conductive member 28. Alternatively, braided conductive member 28 can be constructed of one or more temperature sensors themselves.

Figure 8:
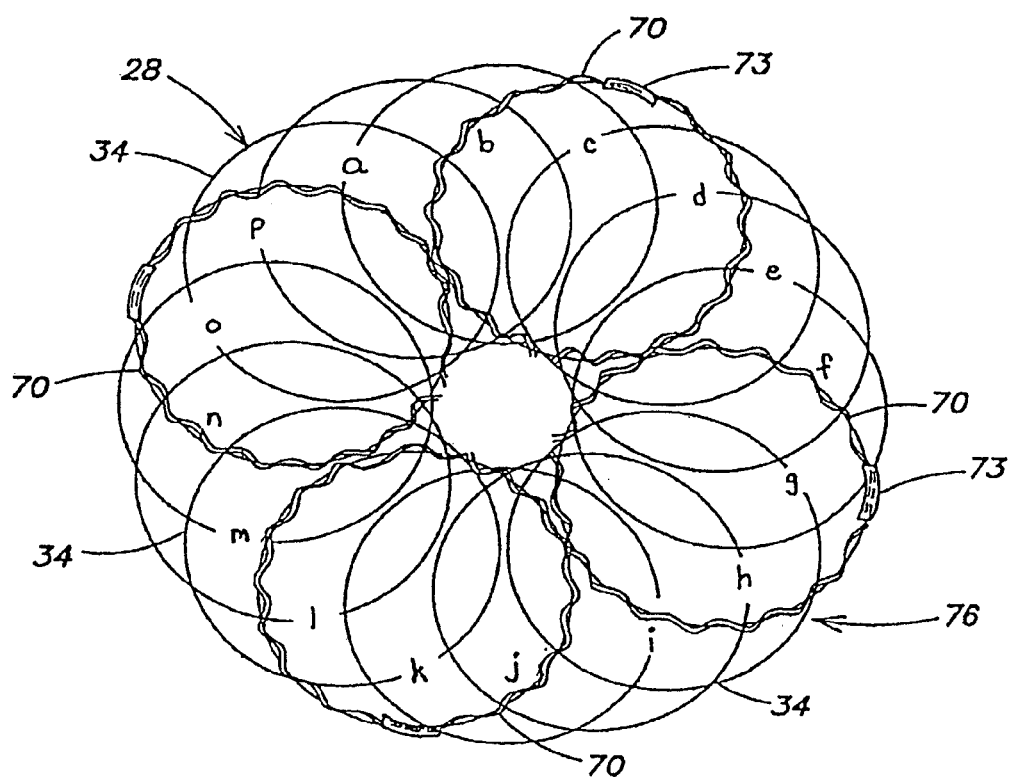
FIGS. 8-10A illustrate, among other things, temperature sensing.

FIG. 8 illustrates braided conductive member 28 in its fully expanded or deployed configuration. Braided conductive member 28 forms a disk when filly expanded. In the embodiment illustrated in FIG. 8, there are sixteen filaments 34 that make up braided conductive member 28.

Temperature monitoring or control can be incorporated into braided conductive member 28, for example, by placing temperature sensors (such as thermocouples, thermistors, etc.) on the expanded braided conductive member 28 such that they are located on the distally facing ablative ring formed when braided conductive member 28 is in its fully expanded configuration. "Temperature monitoring" refers to temperature reporting and display for physician interaction. "Temperature control" refers to the capability of adding an algorithm in a feedback loop to titrate power based on temperature readings from the temperature sensors disposed on braided conductive member 28. Temperature sensors can provide a means of temperature control provided the segment of the ablative ring associated with each sensor is independently controllable (e.g., electrically isolated from other regions of the mesh). For example, control can be achieved by dividing the ablative structure into electrically independent sectors, each with a temperature sensor, or alternatively, each with a mechanism to measure impedance in order to facilitate power titration. The ablative structure may be divided into electrically independent sectors so as to provide zone control. The provision of such sectors can be used to provide power control to various sections of braided conductive member 28.

Figure 9:
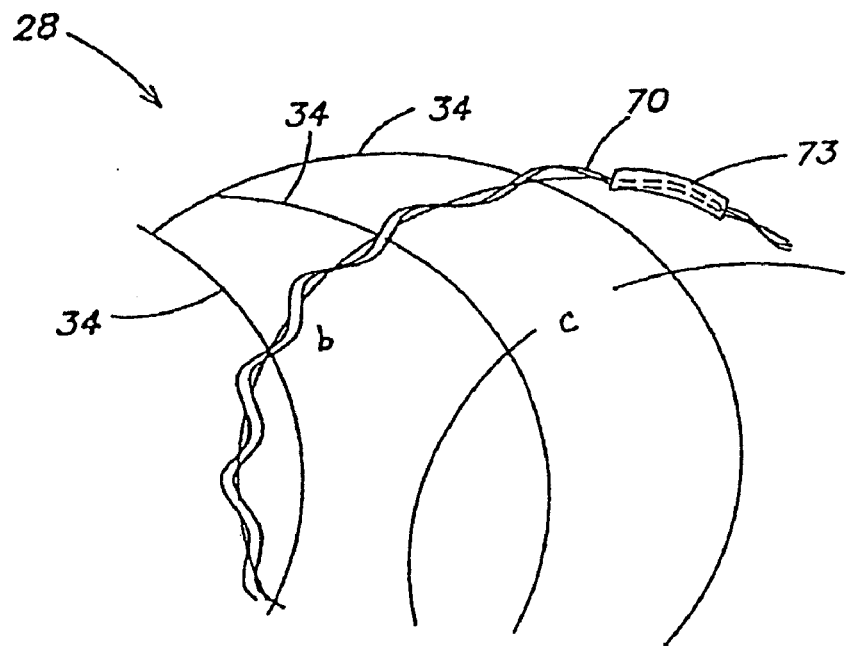

Reference is now made to FIGS. 8-9. As illustrated in FIG. 8, four temperature sensors 70 are provided on braided conductive member 28. As noted previously, since the individual filaments 34 (34a-34p in FIG. 8) in braided conductive member 28 are insulated from each other, a number of independent sectors may be provided. A sector may include one or more filaments 34. During ablation procedures, energy can be applied to one or more of the filaments 34 in any combination desired depending upon the goals of the ablation procedure. A temperature sensor could be provided on each filament 34 of braided conductive member 28 or shared among one or more filaments. In mapping applications, one or more of the filaments 34 can be grouped together for purposes of measuring electrical activity. These sectoring functions can be provided in controller 8.

Figure 10:
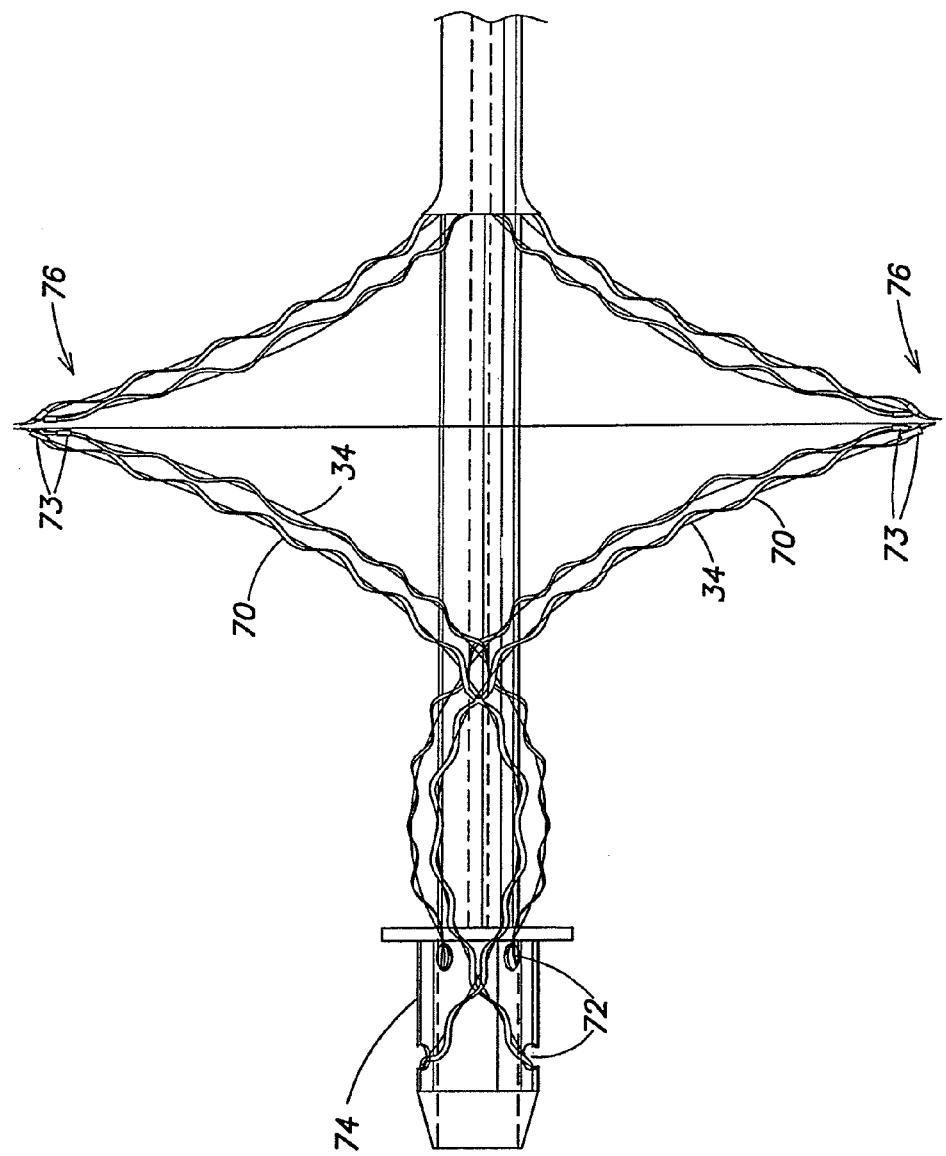

FIG. 10 illustrates a side view of braided conductive member 28 including temperature sensors 70. As shown in FIG. 10, temperature sensors 70 emerge from four holes 72. Each hole 72 is disposed in one quadrant of anchor 74. The temperature sensors 70 are bonded to the outside edge 76 of braided conductive member 28. Temperature sensors 70 may be isolated by a small piece of polyimide tubing 73 around them and then bonded in place to the filaments. The temperature sensors 70 may be woven and twisted into braided conductive member 28 or they can be bonded in a side-by-side or parallel manner with the filaments 34.

There are several methods of implementing electrically independent sectors. In one embodiment, the wires are preferably stripped of their insulative coating in the region forming the ablative ring (when expanded). However, sufficient insulation may be left on the wires in order to prevent interconnection when in the expanded state. Alternatively, adjacent mesh wires can be permitted to touch in their stripped region, but can be separated into groups by fully insulated (unstripped) wires imposed, for example, every 3 or 5 wires apart (the number of wires does not limit this invention), thus forming sectors of independently controllable zones. Each zone can have its own temperature sensor. The wires can be "bundled" (or independently attached) to independent outputs of an ablation energy generator. RF energy can then be titrated in its application to each zone by switching power on and off (and applying power to other zones during the 'off period') or by modulating voltage or current to the zone (in the case of independent controllers). In either case, the temperature inputs from the temperature sensors can be used in a standard feedback algorithm to control the power delivery.

Figure 10A:
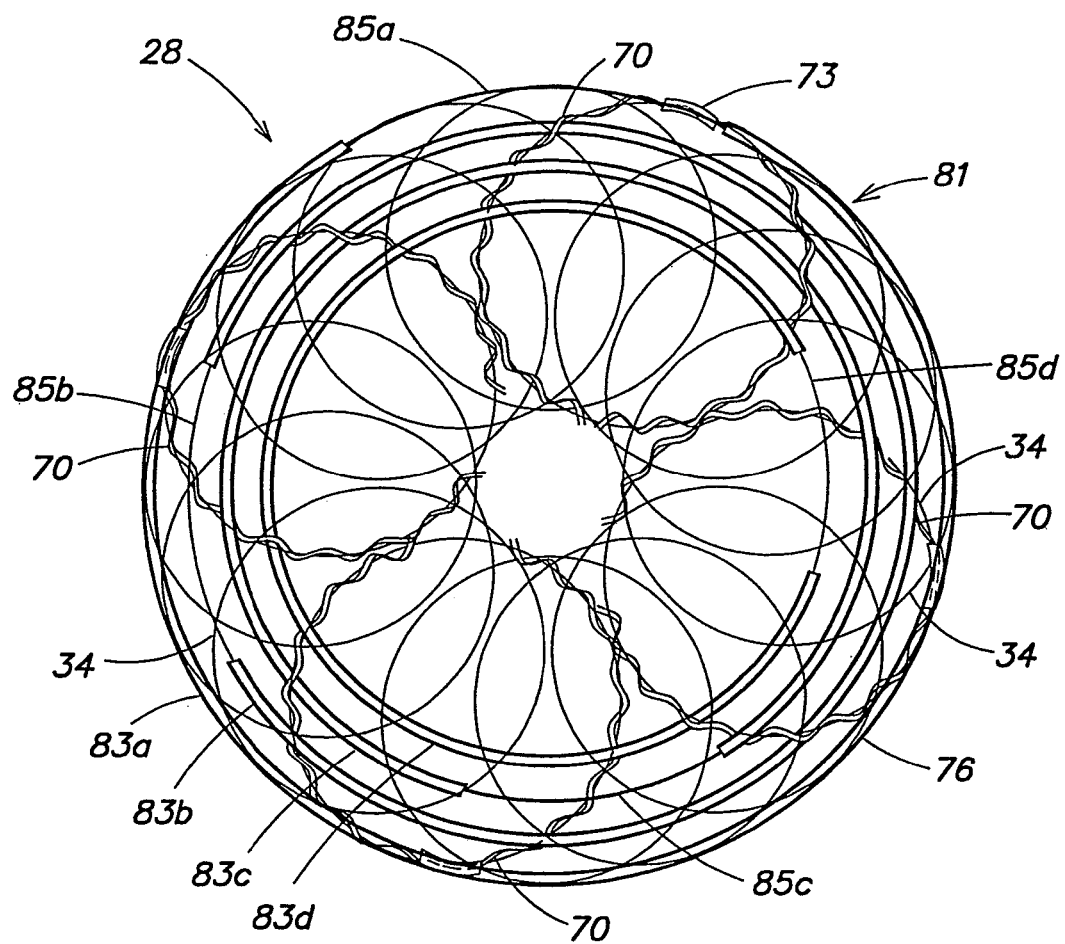

Alternatively, as illustrated in FIG. 10A, braided conductive member 28 may be used to support a ribbon-like structure which is separated into discrete sectors. As shown in FIG. 10A, the ribbon-like structure 81 may be, for example, a pleated copper flat wire that, as braided conductive member 28 expands, unfolds into an annular ring. Each of the wires 83a-83d lie in the same plane. Although four wires are illustrated in FIG. 10A, structure 81 may include any number of wires depending upon the application and desired performance. Each of wires 83a-83d is insulated. Insulation may then be removed from each wire to create different sectors 85a-85d. Alternatively, each of wires 83a-83d may be uninsulated and insulation may be added to create different sectors. The different sectors may provide an ablative zone comprised of independently controllable wires 83*a*-83*d*. Temperature sensors 70 may be mounted on the individual wires, and filaments 34 may be connected to respective wires 83*a*-83*d* to provide independent control of energy to each individual sector. One skilled in the art will appreciate that each of wires 83*a*-83*d* can have multiple sectors formed by removing insulation in various locations and that numerous combinations of sectors 85*a*-85*d* and wires 83*a*-83*d* forming ribbon-like structure 81 can be obtained.

Further, according to the invention, some of sectors 85*a*-85*d* or wires 83*a*-83*d* may be used for mapping or electrical measurement, while other of these sectors 85*a*-85*d* or wires 83*a*-83*d* may be used for ablation. The mapping and ablations sectors and/or wires may be activated independently, and may be activated concurrently, if desired. One application of dedicating some sectors and/or wires for mapping and others for ablation is that a lesion may be formed and the quality of the lesion may be measured using a single braided conductive member 28. This can avoid the need to change catheters during a procedure. Thus, a single catheter may be used for both mapping and ablation.

The quality of a lesion may be determined by a measurement of the impedance of the ablated tissue or by a measurement of the electrical signal strength at the ablated tissue. Impedance of the tissue may be determined by measuring the resistance between any two sectors 85*a*-85*d* or wires 83*a*-83*d* dedicated to mapping based on a known input voltage or current. Ablated tissue has a higher impedance than healthy tissue; thus, a higher impedance value is indicative of a higher degree of ablation. Electrical signal strength may be a unipolar measurement based on a single sector 85*a*-85*d* or wire 83*a*-83*d*. If a measurement of a signal is detected in healthy tissue, the signal will have a higher amplitude than a signal that is detected in ablated tissue. Accordingly, a determination may be made as to the health of the tissue, or quality of the lesion.

Measurement of the impedance of the ablated tissue or measurement of the electrical signal strength at the ablated tissue, described above, may also be performed with other embodiments of the catheter 10 described herein. For example, in the embodiment of FIG. 8., one or more of the sixteen filaments 34 may be used to measure the signal strength of the ablated tissue. For example, a single filament 34 that is isolated from the other filaments or a group of electrically connected filaments may be used. Multiple measurements of the signal strength may be taken in different regions of the braided conductive member 28 and compared to assess the signal strength in different regions or quadrants of the braided conductive member 28. Similarly, any two of the sixteen filaments 34 of FIG. 8 or any two groups of electrically connected filaments, may be used to measure the signal strength of the ablated tissue to measure the impedance between each of the two filaments 34 or groups of filaments.

Either of the impedance measurement or the signal strength measurement may be performed independently by various sectors 85*a*-85*d* or wires 83*a*-83*d* of the braided conductive member. This allows an assessment of lesion quality to be performed for different regions of a lesion, corresponding to different quadrants of the braided conductive member 28.

Steering

Figure 13:
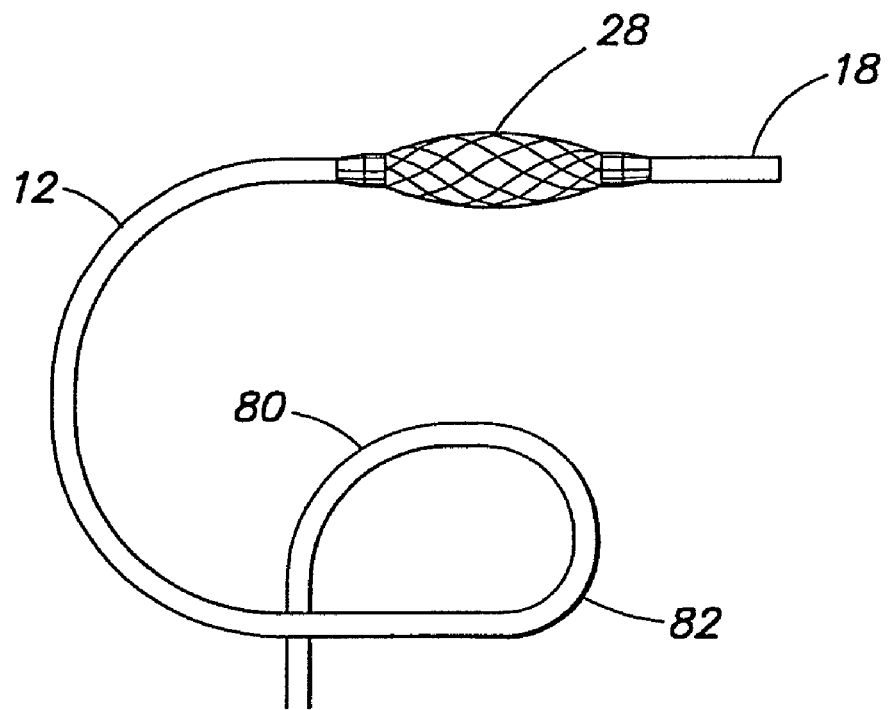

Reference is now made to FIGS. 11-13 which illustrate aspects of the steering capabilities of the present invention. As illustrated in FIGS. 1-2, catheter 10 is capable of being steered using control handle 14. In particular, FIG. 2 illustrates steering where the steering pivot or knuckle is disposed on catheter shaft 12 in a region that is distal to the braided conductive member 28.

FIG. 11 illustrates catheter 10 wherein the pivot point or steering knuckle is disposed proximal to braided conductive member 28.

FIG. 12 illustrates catheter 10 having the capability of providing steering knuckles both proximal and distal to braided conductive member 28.

FIGS. 2 and 11-12 illustrate two dimensional or single plane type steering. The catheter of the present invention can also be used in connection with a three dimensional steering mechanism. For example, using the control handle in the incorporated by reference '852 patent, the catheter can be manipulated into a three-dimensional "lasso-like" shape, particularly at the distal end of the catheter. As shown in FIG. 13, the catheter can have a primary curve 80 in one plane and then a second curve 82 in another plane at an angle to the first plane. With this configuration, the catheter can provide increased access to difficult to reach anatomical structures. For example, a target site for a mapping or ablation operation may be internal to a blood vessel. Thus, the increased steering capability can allow easier access into the target blood vessel. In addition, the additional dimension of steering can allow for better placement of braided conductive member 28 during an ablation or mapping procedure. Catheter 10 can be inserted into a site using the steering capabilities provided by primary curve 80. Thereafter, using the secondary curve 82, braided conductive member 28 can be tilted into another plane for better orientation or contact with the target site.

Conductive Member Configurations And Materials

Reference is now made to FIGS. 14-17 which figures illustrate other configurations of braided conductive member 28. As has been described above and will be described in more detail, braided conductive member 28 can include from one to 300 or more filaments. The filaments may vary from very fine wires having small diameters or cross-sectional areas to large wires having relatively large diameters or cross-sectional areas.

Figure 14:
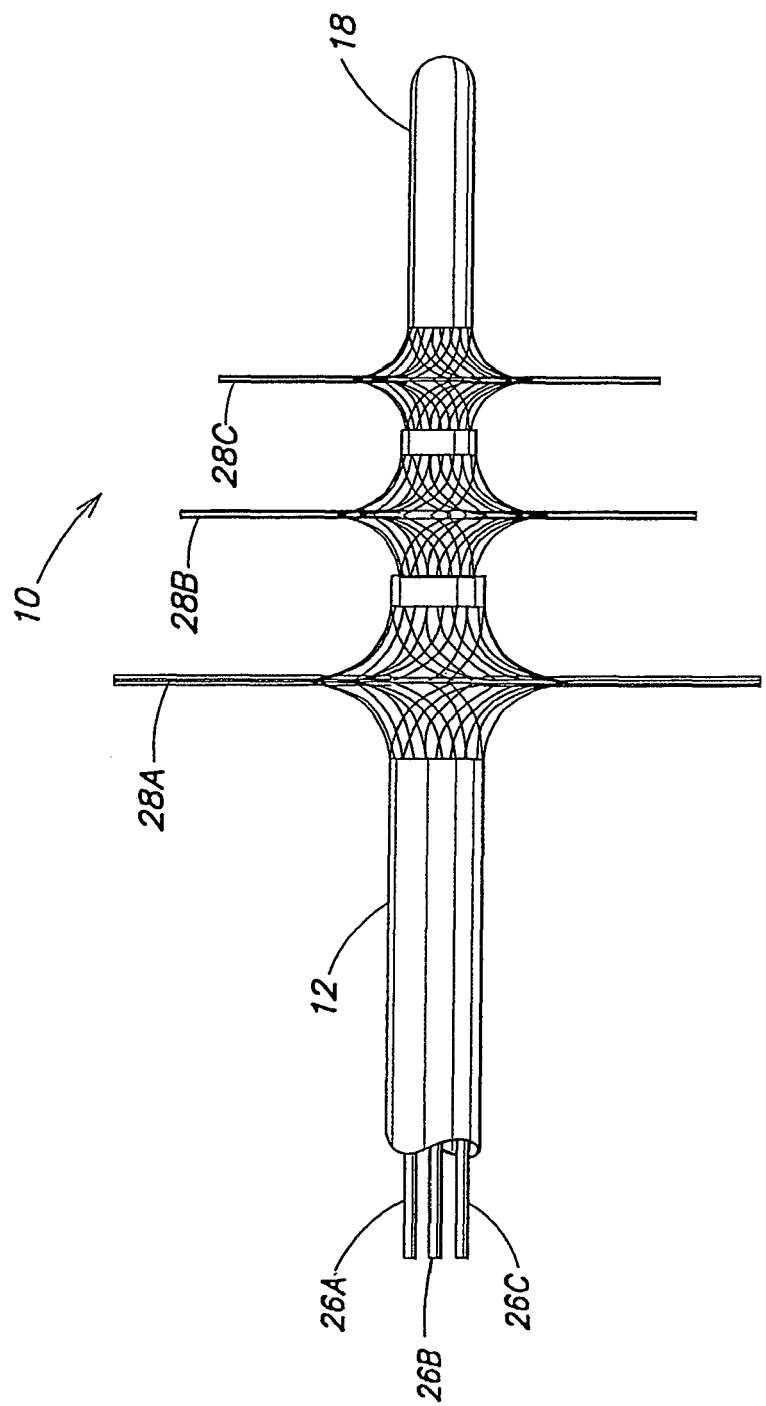
FIGS. 14-17 illustrate further embodiments of the braided conductive member.

FIG. 14 illustrates the use of more than one braided conductive member 28 at the distal end of catheter 10. As shown in FIG. 14, three braided conductive members 28A, 28B, and 28C are provided at the distal end of catheter 10. Braided conductive members 28A, 28B, and 28C may be, in their expanded conditions, the same size or different sizes. Each of the braided conductive members 28A, 28B, and 28C can be expanded or contracted independently in the manner illustrated in FIGS. 1-4 via independent control shafts 26A, 26B, and 26C. The use of multiple braided conductive members provides several advantages. Rather than having to estimate or guess as to the size of the blood vessel prior to starting a mapping or ablation procedure, if braided conductive members 28A, 28B, and 28C are of different expanded diameters, than sizing can be done in vivo during a procedure. In addition, one of the braided conductive members can be used for ablation and another of the braided conductive members can be used for mapping. This allows for quickly checking the effectiveness of an ablation procedure.

Figure 15A:
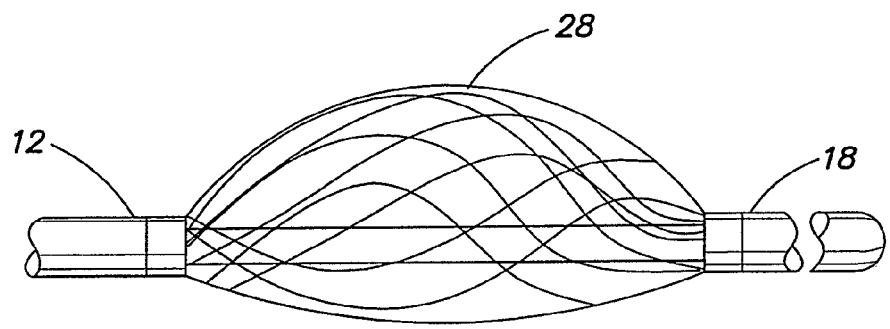
Figure 15B:
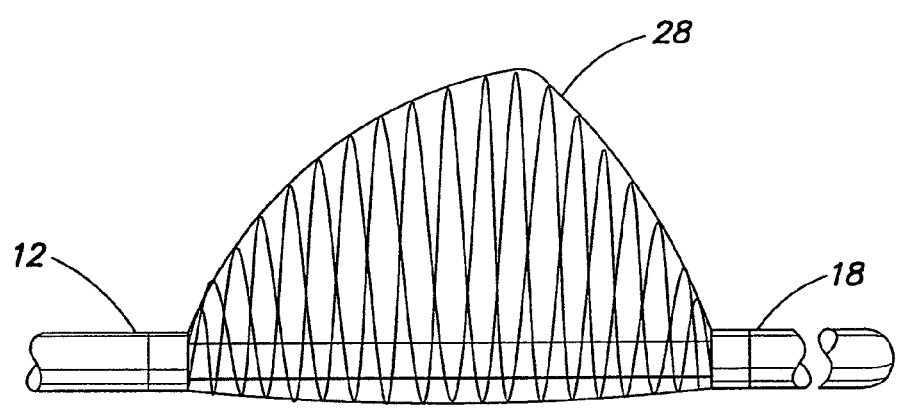

Reference is now made to FIG. 15A and 15B, which figures illustrate other shapes of braided conductive member 28. As described up to this point, braided conductive member 28 is generally symmetrical and coaxial with respect to catheter shaft 12. However, certain anatomical structures may have complex three-dimensional shapes that are not easily approximated by a geometrically symmetrical mapping or ablation structure. One example of this type of structure occurs at the CS ostium. To successfully contact these types of anatomical structures, braided conductive member 28 can be "preformed" to a close approximation of that anatomy, and yet still be flexible enough to adapt to variations found in specific patients. Alternatively, braided conductive member 28 can be "preformed" to a close approximation of that anatomy, and be of sufficient strength (as by choice of materials, configuration, etc.) to force the tissue to conform to variations found in specific patients. For example, FIG. 15A illustrates braided conductive member 28 disposed about shaft 12 in an off-center or non-concentric manner. In addition, braided conductive member 28 may be constructed so that the parameter of the braided conductive member 28 in its expanded configuration has a non-circular edge so as to improve tissue contact around the parameter of the braided conductive member. FIG. 15B illustrates an example of this type of configuration where the braided conductive member 28 is both off center or non concentric with respect to catheter shaft 12 and also, in its deployed or expanded configuration, has an asymmetric shape. The eccentricity of braided conductive member 28 with respect to the shaft and the asymmetric deployed configurations can be produced by providing additional structural supports in braided conductive member 28, for example, such as by adding nitinol, ribbon wire, and so on. In addition, varying the winding pitch or individual filament size or placement or deforming selective filaments in braided conductive member 28 or any other means known to those skilled in the art may be used.

Figure 16A:
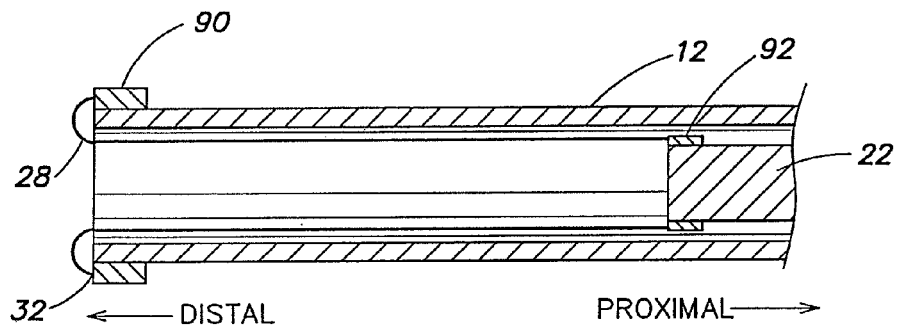
Figure 16B:
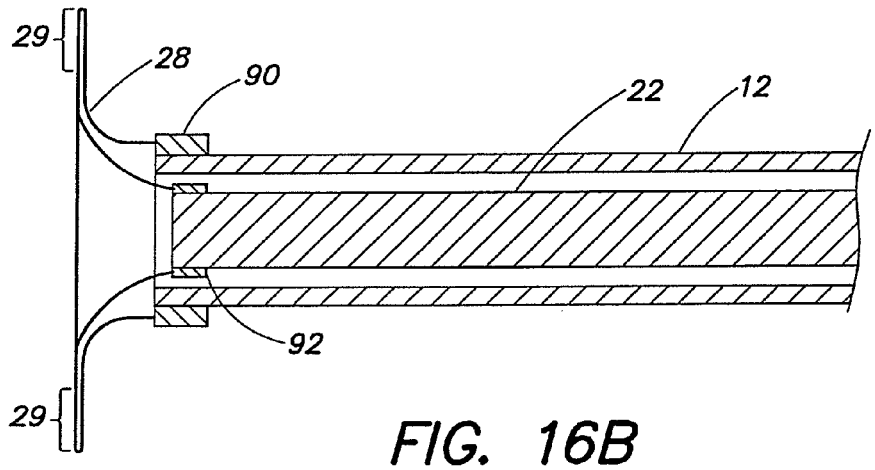
Figure 16C:
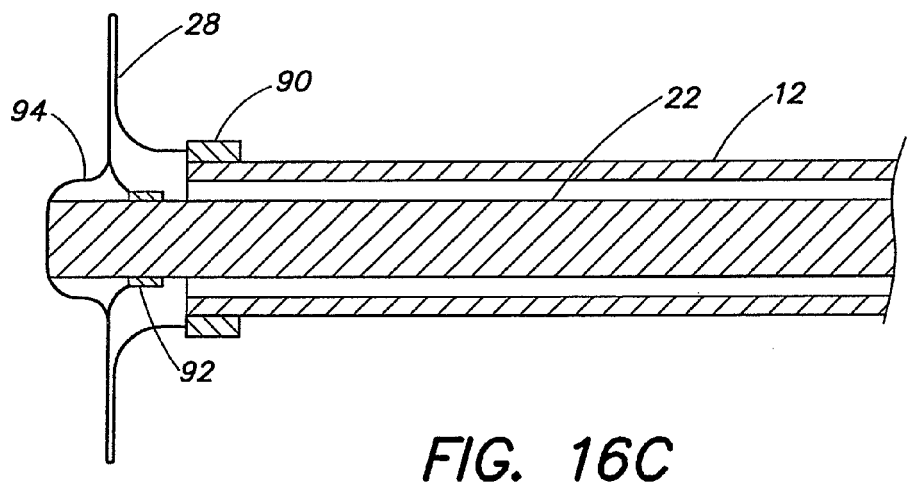

FIGS. 16A-16C illustrate another configuration of braided conductive member 28 and catheter 10. As illustrated in FIGS. 16A-16C, the distal tip section of catheter 10 has been removed and braided conductive member 28 is disposed at the distal end of catheter 10. One end of braided conductive member 28 is anchored to catheter shaft 12 using an anchor band 90 that clamps the end 32 of braided conductive member 28 to catheter shaft 12. The other end of braided conductive member 28 is clamped to an activating shaft such as shaft 26 using another anchor band 92. FIG. 16A illustrates braided conductive member 28 in its undeployed configuration. As shaft 22 is moved distally, braided conductive member 28 emerges or everts from shaft 12. As shown in FIG. 16B, braided conductive member 28 has reached its fully deployed diameter and an annular tissue contact zone 29 can be placed against an ostium or other anatomical structure. As illustrated in FIG. 16C, further distal movement of shaft 22 can be used to create a concentric locating region 94 that can help to provide for concentric placement within an ostium of a pulmonary vein, for example. Concentric locating region 94 may be formed by selective variations in the winding density of filaments 34 in braided conductive member 28, preferential predeformation of the filaments, additional eversion of braided conductive member 28 from shaft 12, or by other means known to those skilled in the art.

Figure 17:
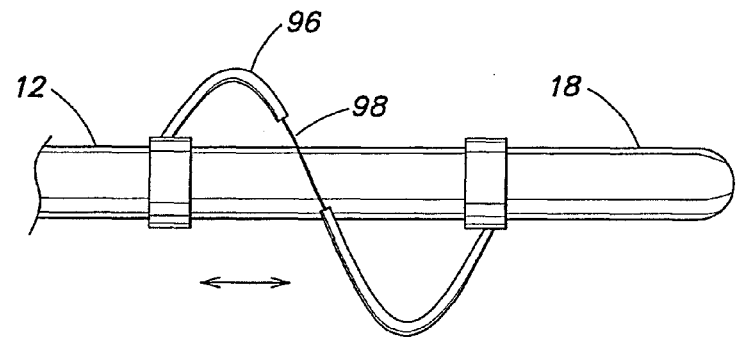

Reference is now made to FIG. 17, which figure illustrates a further embodiment of braided conductive member 28. As illustrated in FIG. 17, braided conductive member 28 is composed of one or several large wires 96 rather than a multiplicity of smaller diameter wires. The wire or wires can be moved between the expanded and unexpanded positions in the same manner as illustrated in FIG. 1. In addition, a region 98 may be provided in which the insulation has been removed for mapping or ablation procedures. The single wire or "corkscrew" configuration provides several advantages. First, the wire or wires do not cross each other and therefore there is only a single winding direction required for manufacture. In addition, the risk of thrombogenicity may be reduced because there is a smaller area of the blood vessel being blocked. In addition, the connections between the ends of the large wire and the control shafts may be simplified.

The catheter 10 of the present invention can be coated with a number of coatings that can enhance the operating properties of braided conductive member 28. The coatings can be applied by any of a number of techniques and the coatings may include a wide range of polymers and other materials.

Braided conductive member 28 can be coated to reduce its coefficient of friction, thus reducing the possibility of thrombi adhesion to the braided conductive member as well as the possibility of vascular or atrial damage. These coatings can be combined with the insulation on the filaments that make up braided conductive member 28, these coatings can be included in the insulation itself, or the coatings can be applied on top of the insulation. Examples of coating materials that can be used to improve the lubricity of the catheter include PD slick available from Phelps Dodge Corporation, Ag, Tin, BN. These materials can be applied by an ion beam assisted deposition ("IBAD") technique developed by, for example, Amp Corporation.

Braided conductive member 28 can also be coated to increase or decrease its thermal conduction which can improve the safety or efficacy of the braided conductive member 28. This may be achieved by incorporating thermally conductive elements into the electrical insulation of the filaments that make up braided conductive member 28 or as an added coating to the assembly. Alternatively, thermally insulating elements may be incorporated into the electrical insulation of the filaments that make up braided conductive member 28 or added as a coating to the assembly. Polymer mixing, IBAD, or similar technology could be used to add Ag, Pt, Pd, Au, Ir, Cobalt, and others into the insulation or to coat braided conductive member 28.

Radiopaque coatings or markers can also be used to provide a reference point for orientation of braided conductive member 28 when viewed during fluoroscopic imaging. The materials that provide radiopacity including, for example, Au, Pt, Ir, and other known to those skilled in the art. These materials may be incorporated and used as coatings as described above.

Antithrombogenic coatings, such as heparin and BH, can also be applied to braided conductive member 28 to reduce thrombogenicity to prevent blood aggregation on braided conductive member 28. These coatings can be applied by dipping or spraying, for example.

As noted above, the filament 34 of braided conductive member 28 may be constructed of metal wire materials. These materials may be, for example, MP35N, nitinol, or stainless steel. Filaments 34 may also be composites of these materials in combination with a core of another material such as silver or platinum. The combination of a highly conductive electrical core material with another material forming the shell of the wire allows the mechanical properties of the shell material to be combined with the electrical conductivity of the core material to achieve better and/or selectable performance. The choice and percentage of core material used in combination with the choice and percentage of shell material used can be selected based on the desired performance characteristics and mechanical/electrical properties desired for a particular application.

Irrigation

It is known that for a given electrode side and tissue contact area, the size of a lesion created by radiofrequency (RF) energy is a function of the RF power level and the exposure time. At higher powers, however, the exposure time can be limited by an increase in impedance that occurs when the temperature at the electrode-tissue interface approaches 100°

Figure 18:
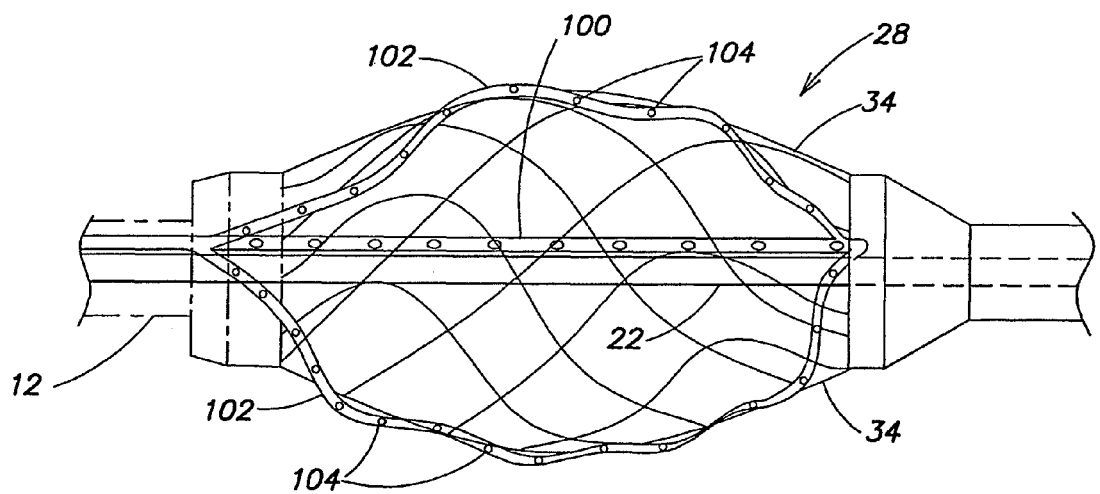

C. One way of maintaining the temperature less than or equal to this limit is to irrigate the ablation electrode with saline to provide convective cooling so as to control the electrode-tissue interface temperature and thereby prevent an increase in impedance. Accordingly, irrigation of braided conductive member 28 and the tissue site at which a lesion is to be created can be provided in the present invention. FIG. 18 illustrates the use of an irrigation manifold within braided conductive member 28. An irrigation manifold 100 is disposed along shaft 22 inside braided conductive member 28. Irrigation manifold 100 may be one or more polyimid tubes. Within braided conductive member 28, the irrigation manifold splits into a number of smaller tubes 102 that are woven into braided conductive member 28 along a respective filament 34. A series of holes 104 may be provided in each of the tubes 102. These holes can be oriented in any number of ways to target a specific site or portion of braided conductive member 28 for irrigation. Irrigation manifold 100 runs through catheter shaft 12 and may be connected to an irrigation delivery device outside the patient used to inject an irrigation fluid, such as saline, for example, such as during an ablation procedure.

The irrigation system can also be used to deliver a contrast fluid for verifying location or changes in vessel diameter. For example, a contrast medium may be perfused prior to ablation and then after an ablation procedure to verify that there have been no changes in the blood vessel diameter. The contrast medium can also be used during mapping procedures to verify placement of braided conductive member 28. In either ablation or mapping procedures, antithrombogenic fluids, such as heparin can also be perfused to reduce thrombogenicity.

FIGS. 19 and 19A illustrate another way of providing perfusion/irrigation in catheter 10. As illustrated in FIGS. 19 and 19A, the filaments 34 that comprise braided conductive member 28 are composed of a composite wire 110. The composite wire 110 includes an electrically conductive wire 112 that is used for delivering ablation energy in an ablation procedure or for detecting electrical activity during a mapping procedure. Electrical wire 112 is contained within a lumen 114 that also contains a perfusion lumen 116. Perfusion lumen 116 is used to deliver irrigation fluid or a contrast fluid as described in connection with FIG. 18. Once braided conductive member 28 has been constructed with composite wire 110, the insulation 118 surrounding wire filament 112 can be stripped away to form an electrode surface. Holes can then be provided into perfusion lumen 116 to then allow perfusion at targeted sites along the electrode surface. As with the embodiment illustrated in FIG. 18, the perfusion lumens can be connected together to form a manifold which manifold can then be connected to, for example, perfusion tube 120 and connected to a fluid delivery device.

Shrouds

The use of a shroud or shrouds to cover at least a portion of braided conductive member 28 can be beneficial in several ways. The shroud can add protection to braided conductive member 28 during insertion and removal of catheter 10. A shroud can also be used to form or shape braided conductive member 28 when in its deployed state. Shrouds may also reduce the risk of thrombi formation on braided conductive member 28 by reducing the area of filament and the number of filament crossings exposed to blood contact. This can be particularly beneficial at the ends 30 and 32 of braided conductive member 28. The density of filaments at ends 30 and 32 is greatest and the ends can therefore be prone to blood aggregation. The shrouds can be composed of latex balloon material or any material that would be resistant to thrombi formation durable enough to survive insertion through an introducer system, and would not reduce the mobility of braided conductive member 28. The shrouds can also be composed of an RF transparent material that would allow RF energy to pass through the shroud. If an RF transparent material is used, complete encapsulation of braided conductive member 28 is possible.

A shroud or shrouds may also be useful when irrigation or perfusion is used, since the shrouds can act to direct irrigation or contrast fluid to a target region.

Figure 20A:
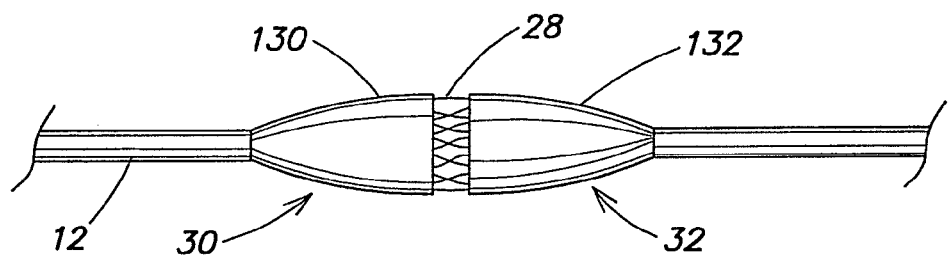
FIGS. 20A-20E illustrate the use of shrouds.
Figure 20B:
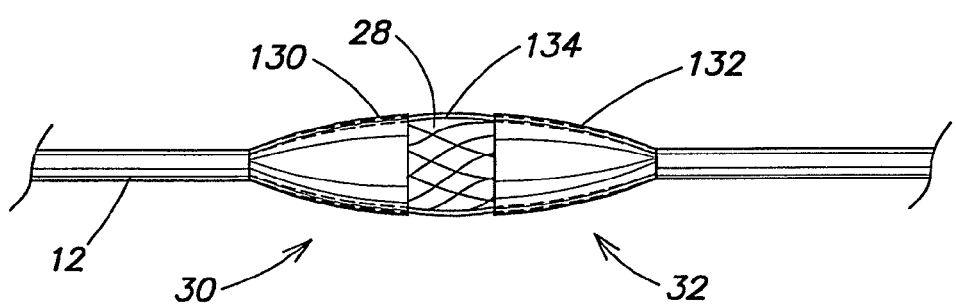

FIGS. 20A-20E illustrate various examples of shrouds that may be used in the present invention. FIG. 20A illustrates shrouds 130 and 132 disposed over end regions 30 and 32, respectively, of braided conductive member 28. This configuration can be useful in preventing coagulation of blood at the ends of braided conductive member 28. FIG. 20B illustrates shrouds 130 and 132 used in conjunction with an internal shroud 134 contained inside braided conductive member 28. In addition to preventing blood coagulation in regions 30 and 32, the embodiment illustrated in FIG. 20B also prevents blood from entering braided conductive member 28.

Figure 20C:
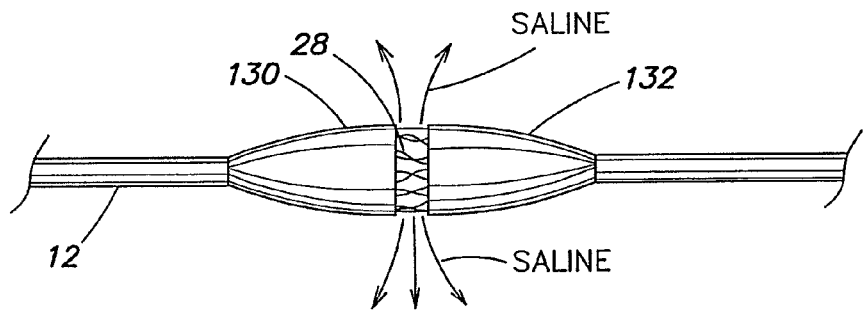

FIG. 20C illustrates shrouds 130 and 132 being used to direct and irrigation fluid or contrast medium along the circumferential edge of braided conductive member 28. In the embodiment illustrated in FIG. 20C, perfusion can be provided as illustrated in FIGS. 18 and 19.

Figure 20D:
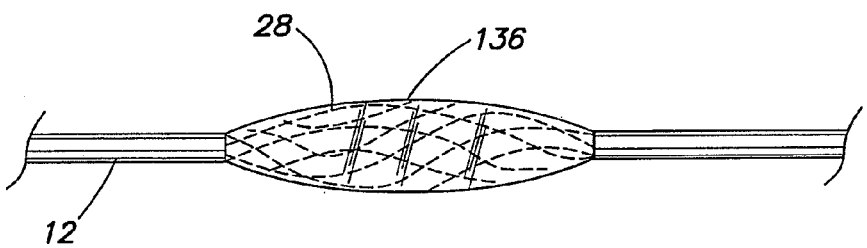

FIG. 20D illustrates the use of an external shroud that covers braided conductive member 28. Shroud 136 completely encases braided conductive member 28 and thereby eliminates blood contact with braided conductive member 28. Shroud 136 may be constructed of a flexible yet ablation-energy transparent material so that, when used in an ablation procedure, braided conductive member 28 can still deliver energy to a targeted ablation site.

Figure 20E:
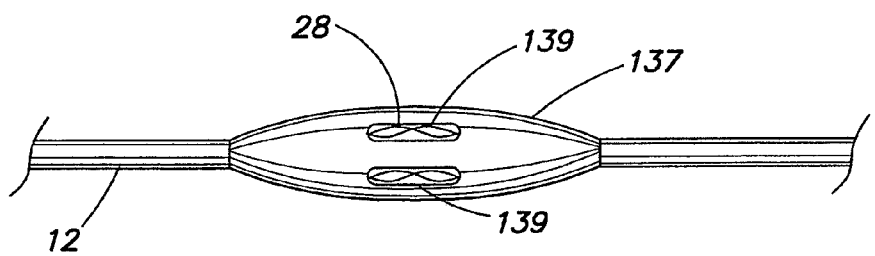

FIG. 20E also illustrates an external shroud 137 encasing braided conductive member 28. Shroud 137 may also be constructed of a flexible yet ablation-energy transparent material. Openings 139 may be provided in shroud 137 to allow the portions of braided conductive member 28 that are exposed by the opening to come into contact with tissue. Openings 139 may be elliptical, circular, circumferential, etc.

Guiding Sheaths

There may be times during ablation or mapping procedures when catheter 10 is passing through difficult or tortuous vasculature. During these times, it may be helpful to have a guiding sheath through which to pass catheter 10 so as to allow easier passage through the patient's vasculature.

Figure 21:
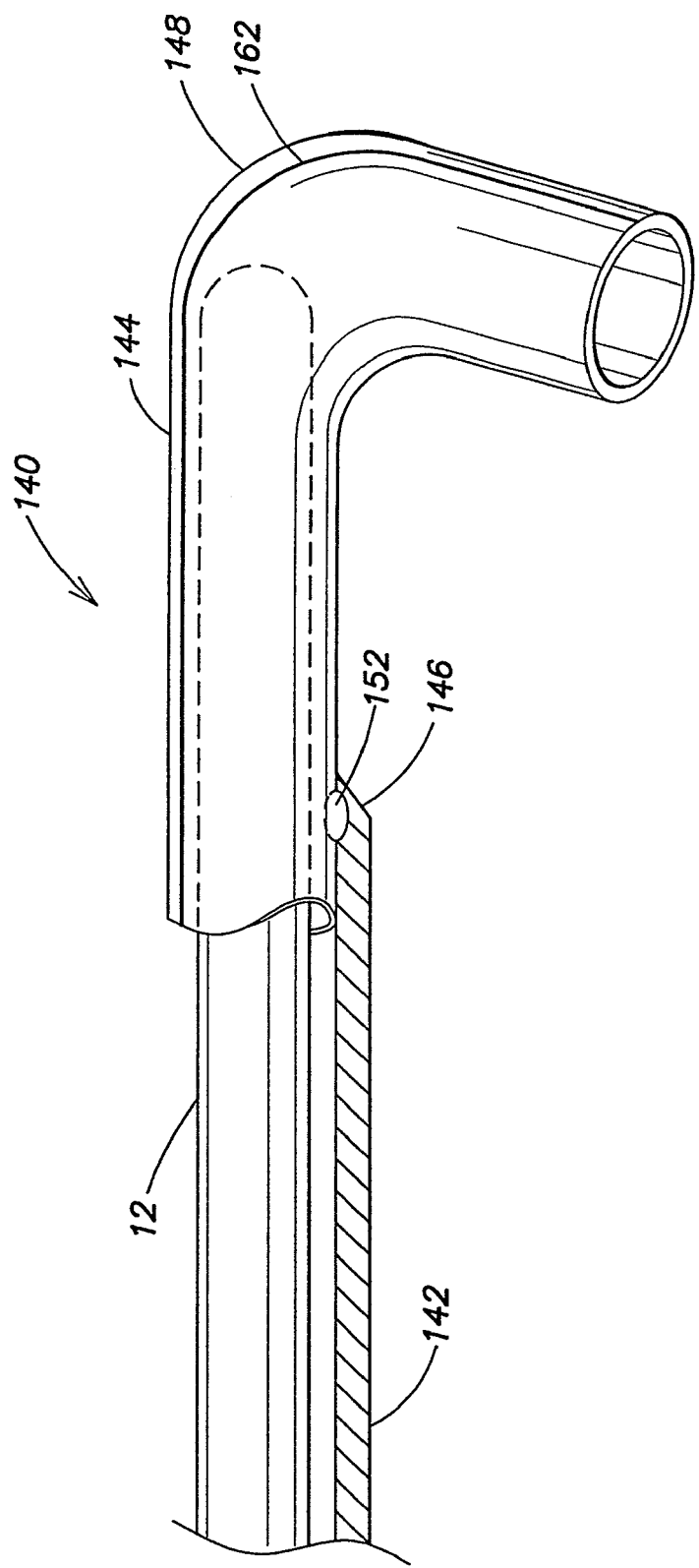
FIG. 21 illustrates a guiding sheath that may be used in connection with the catheter.

FIG. 21 illustrates one example of a guiding sheath that may be used in connection with catheter 10. As illustrated in FIG. 21, the guiding sheath 140 includes a longitudinal member 142. Longitudinal member 142 may be constructed of a material rigid enough to be pushed next to catheter shaft 12 as the catheter is threaded through the vasculature. In one example, longitudinal member 142 may be stainless steel. Longitudinal member 142 is attached to a sheath 144 disposed at the distal end 146 of longitudinal member 142. The split sheath 144 may have one or more predetermined curves 148 that are compatible with the shapes of particular blood vessels (arteries or veins) that catheter 10 needs to pass through. Split sheath 144 may extend proximally along longitudinal member 142. For example, sheath 144 and longitudinal member 142 may be bonded together for a length of up to 20 or 30 centimeters to allow easier passage through the patient's blood vessels. Sheath 144 includes a predetermined region 162 that extends longitudinally along sheath 144. Region 162 may be, for example, a seam, that allows sheath 144 to be split open so that the guiding sheath 140 can be pulled back and peeled off catheter shaft 12 in order to remove the sheath.

In another embodiment, longitudinal member 142 may be a hypotube or the like having an opening 152 at distal end 146 that communicates with the interior of sheath 144. In this embodiment, longitudinal member 142 can be used to inject irrigation fluid such as saline or a contrast medium for purposes of cooling, flushing, or visualization.

Localization Localization refers to a number of techniques whereby the location of catheter 1 in a patient can be determined. Apparatus and methods for localization can be incorporated into catheter 10.

An electromagnetic sensor, used for localization, may be fixed within the shaft of the catheter 10 using any suitable mechanism, such as glue or solder. The electromagnetic sensor generates signals indicative of the location of the electromagnetic sensor. A wire electrically connects the electromagnetic sensor to the controller 8, allowing the generated signals to be transmitted to the controller 8 for processing.

In addition to the electromagnetic sensor fixed to the catheter, a second electromagnetic sensor is provided that is fixed relative to the patient. The second electromagnetic sensor is attached, for example, to the patient's body, and serves as a reference sensor. A magnetic field is also provided, which is exposed to the electromagnetic sensors. Coils within each electromagnetic sensor generate electrical currents when exposed to the magnetic field. The electrical current generated by the coils of each sensor corresponds to a position of each sensor within the magnetic field. Signals generated by the reference electromagnetic sensor and electromagnetic sensor fixed to the catheter are analyzed by the controller 8 to ascertain a precise location of electromagnetic sensor fixed to the catheter 10.

Further, the signals can be used to generate a contour map of the heart. The map may be generated by contacting the catheter 10 with the heart tissue at a number of locations along the heart wall. At each location, the electric signals generated by the electromagnetic sensors are transmitted to the controller 8, or to another processor, to determine and record a location of the catheter 10. The contour map is generated by compiling the location information for each point of contact. This map may be correlated with heart signal data, measured by one or more electrodes on the catheter, for each location to generate a map of both the shape and electrical activity of the heart. Signals generated by the electromagnetic sensors may also be analyzed to determine a displacement of the catheter 10 caused by heartbeat.

As an alternative to the use of electromagnetic sensors other conventional techniques, such as ultrasound or magnetic resonance imaging (MRI) can also be used for localization of catheter 10.

In addition, an impedance-based sensor can also be incorporated into catheter 10. In an impedance-based system, several, such as three, high frequency signals are generated along different axes. The catheter electrodes may be used to sense these frequencies, and with appropriate filtering, the strength of the signal and thus the position of the catheter can be determined.

One skilled in the art will appreciate that the construction of catheter 10 may be optimized to make use of the various localization techniques.

Endocardial and Epicardial Applications

Figure 22:
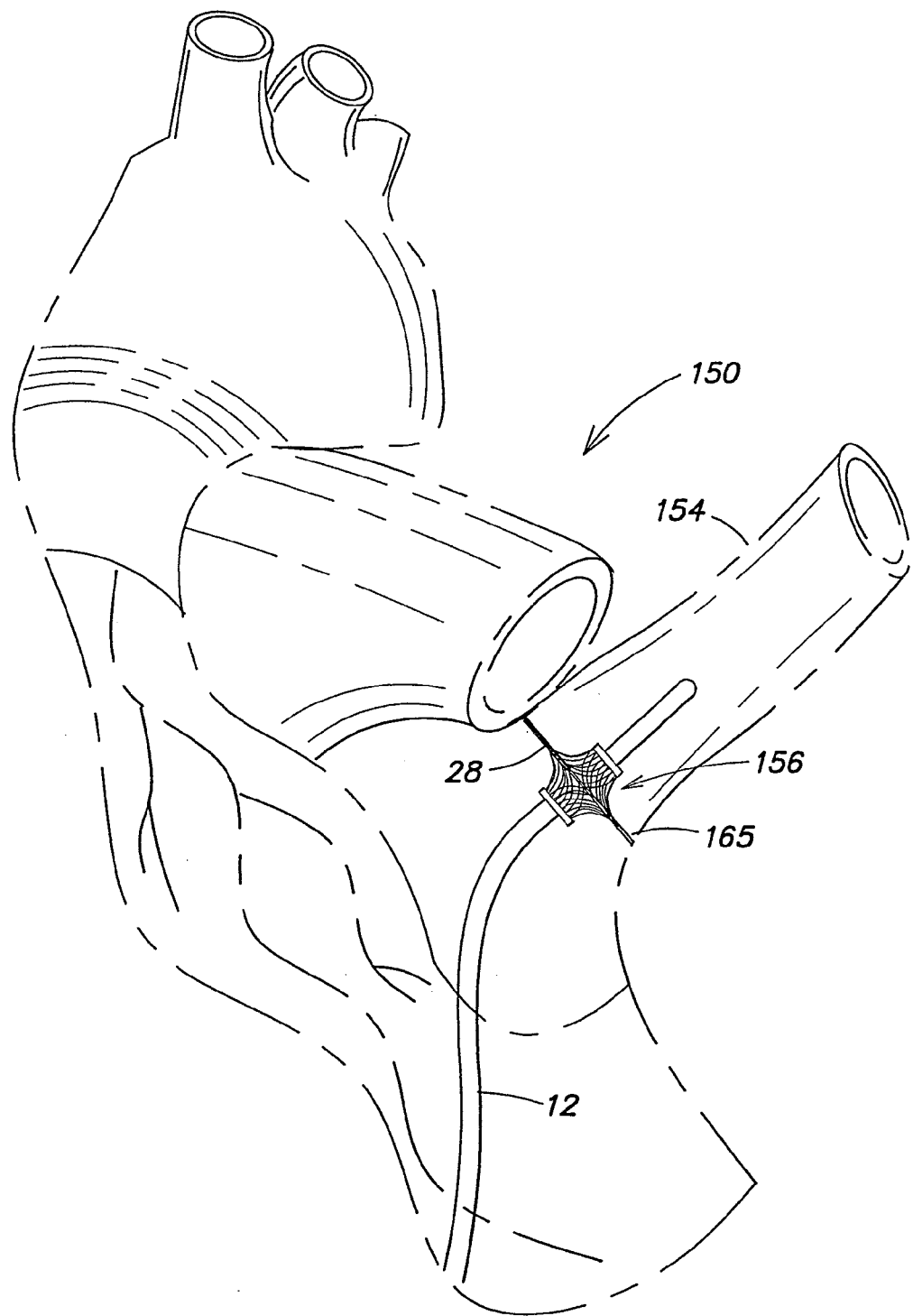
FIGS. 22-31 illustrate methods of using the catheter.
Figure 23:
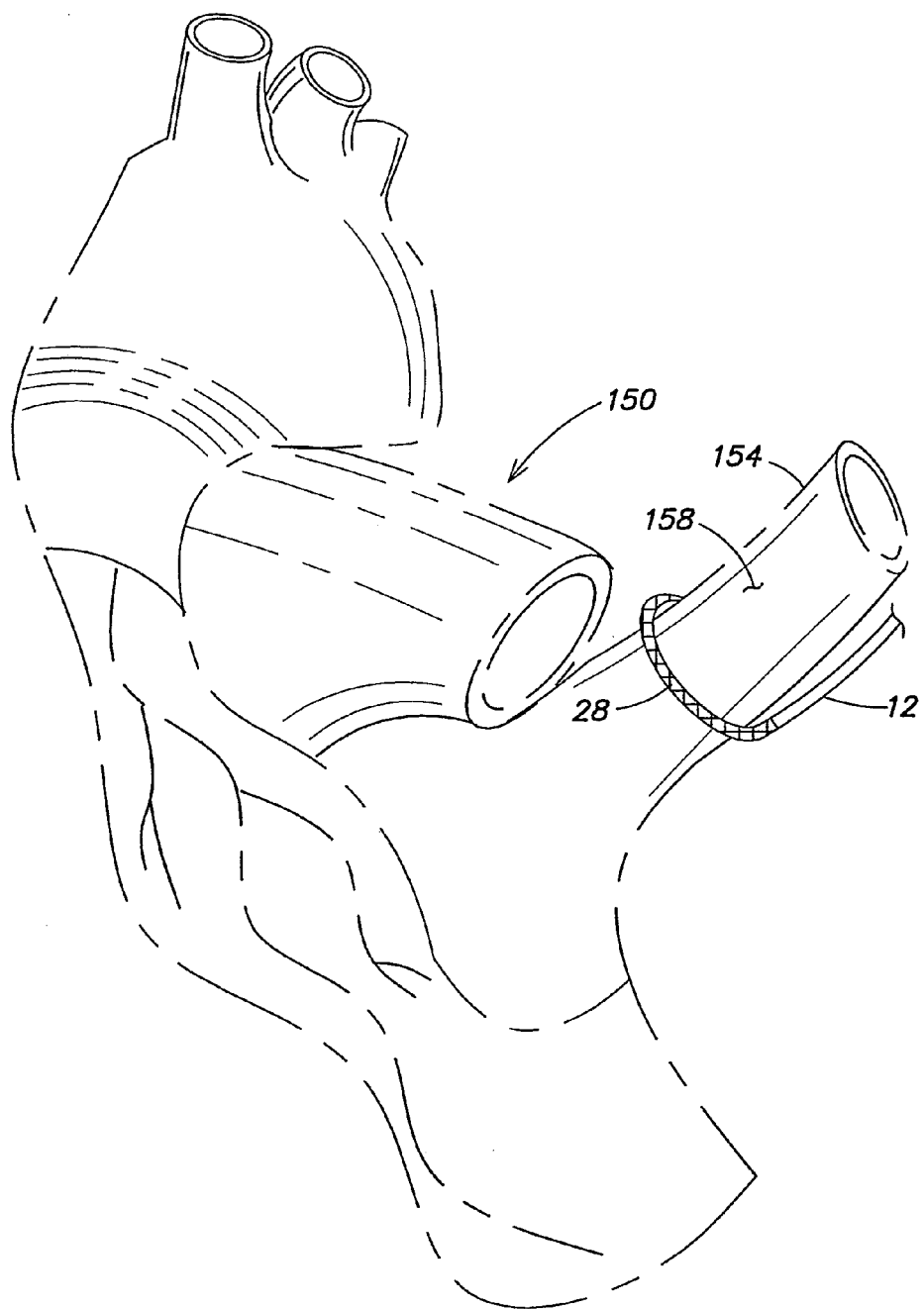
Figure 24:
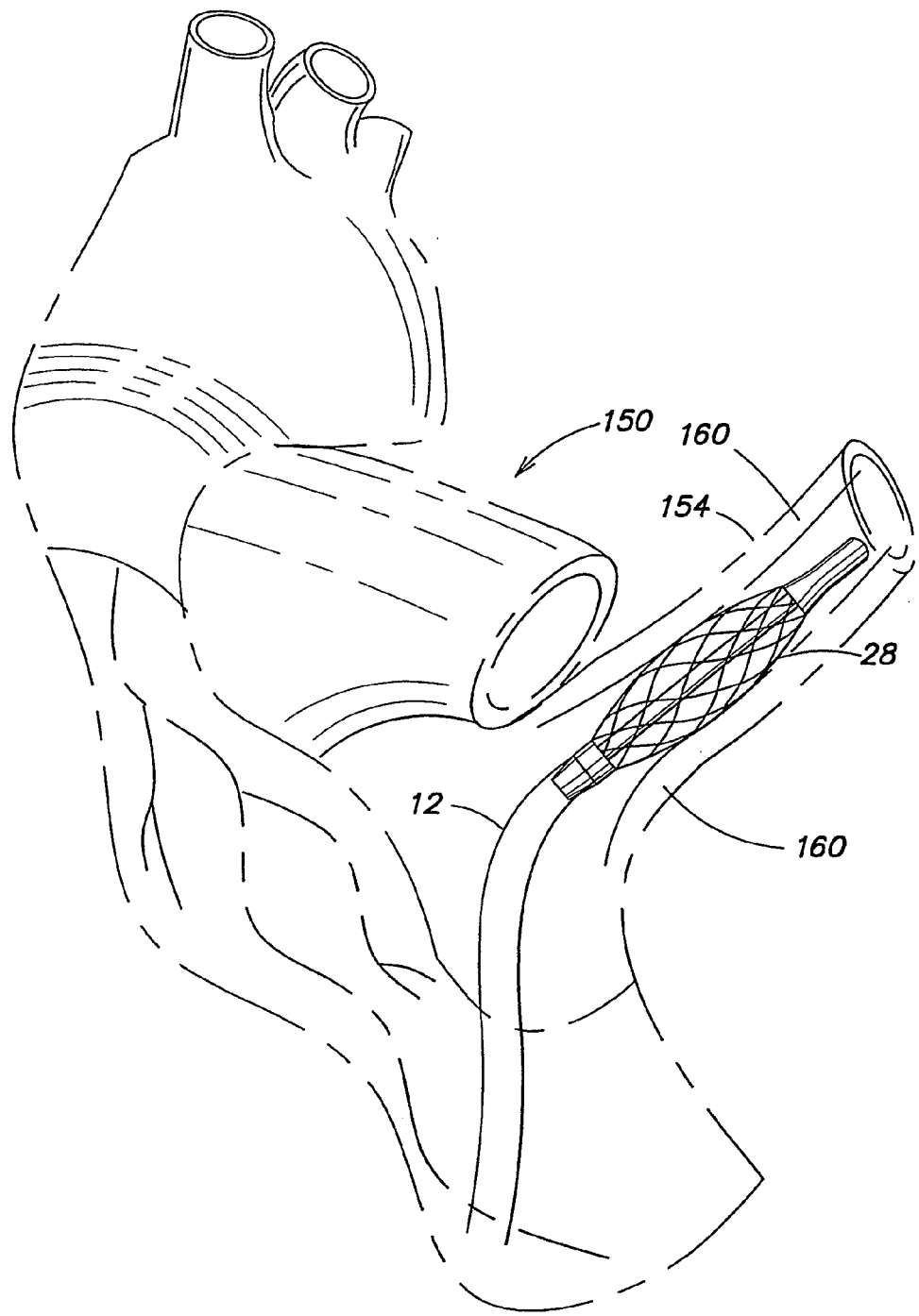

Reference is now made to FIGS. 22, 23, and 24, which figures illustrate how the catheter of the present invention may be used in other endocardial and epicardial applications.

Referring to FIG. 22, this figure illustrates an endocardial ablation procedure. In this procedure, catheter shaft 12 is introduced into a patient's heart 150. Appropriate imaging guidance (direct visual assessment, camera port, fluoroscopy, echocardiographic, magnetic resonance, etc.) can be used. FIG. 22 in particular illustrates catheter shaft 12 being placed in the left atrium of the patient's heart. Once catheter shaft 12 reaches the patient's left atrium, it may then be introduced through an ostium 165 of a pulmonary vein 154. As illustrated, braided conductive member 28 is then expanded to its deployed position, where, in the illustrated embodiment, braided conductive member 28 forms a disk. Catheter shaft 12 is then advanced further into pulmonary vein 154 until the distal side 156 of braided conductive member 28 makes contact with the ostium of pulmonary vein 154. External pressure may be applied along catheter shaft 12 to achieve the desired level of contact of braided conductive member 28 with the ostium tissue. Energy is then applied to the ostium tissue 165 in contact with braided conductive member 28 to create an annular lesion at or near the ostium. The energy used may be RF (radiofrequency), DC, microwave, ultrasonic, cryothermal, optical, etc.

Reference is now made to FIG. 23, which figure illustrates an epicardial ablation procedure. As illustrated in FIG. 23, catheter shaft 12 is introduced into a patient's thoracic cavity and directed to pulmonary vein 154. Catheter 10 may be introduced through a trocar port or intraoperatively during open chest surgery Using a steering mechanism, preformed shape, or other means by which to make contact between braided conductive member 128 and the outer surface 158 of pulmonary vein 154, braided conductive member 28 is brought into contact with the outer surface 158 of pulmonary vein 154. Appropriate imaging guidance (direct visual assessment, camera port, fluoroscopy, echocardiographic, magnetic resonance, etc.) can be used. As illustrated in FIG. 23, in this procedure, braided conductive member 28 remains in its undeployed or unexpanded condition. External pressure maybe applied to achieve contact between braided conductive member 28 with pulmonary vein 154. Once the desired contact with the outer surface 158 of pulmonary vein 154 is attained, ablation energy is applied to surface 158 via braided conductive member 28 using, for example, RF, DC, ultrasound, microwave, cryothermal, or optical energy. Thereafter, braided conductive member 28 may be moved around the circumference of pulmonary vein 154, and the ablation procedure repeated. This procedure may be used to create, for example, an annular lesion at or near the ostium.

Use of the illustrated endocardial or epicardial procedures may be easier and faster than using a single "point" electrode since a complete annular lesion may be created in one application of RF energy.

Reference is now made to FIG. 24 which figure illustrates an endocardial mapping procedure. In the procedure illustrated in FIG. 24, catheter shaft 12 is introduced into pulmonary vein 154 in the manner described in connection with FIG. 22. Once braided conductive 28 has reached a desired location within pulmonary vein 154, braided conductive member 28 is expanded as described in connection with, for example, FIGS. 2-5 until filaments 34 contact the inner wall 160 of pulmonary vein 154. Thereafter, electrical activity within pulmonary vein 154 may be detected, measured, and recorded by an external device connected to the filaments 34 of braided conductive member 28.

Access to the patient's heart can be accomplished via percutaneous, vascular, surgical (e.g. open-chest surgery), or transthoracic approaches for either endocardial or epicardial mapping and/or mapping and ablation procedures.

The present invention is thus able to provide an electrophysiology catheter capable of mapping and/or mapping and ablation operations. In addition, the catheter of the invention may be used to provide high density maps of a tissue region because electrocardiograms may be obtained from individual filaments 34 in braided conductive member 28 in either a bipolar or unipolar mode.

Furthermore, the shape of the electrode region can be adjusted by controlling the radial expansion of braided conductive member 28 SO as to improve conformity with the patient's tissue or to provide a desired mapping or ablation profile. Alternatively, braided conductive member 28 may be fabricated of a material of sufficient flexural strength so that the tissue is preferentially conformed to match the expanded or partially expanded shape of the braided conductive member 28.

The catheter of the present invention may be used for mapping procedures, ablation procedures, and temperature measurement and control on the distal and/or proximal facing sides of braided conductive member 28 in its fully expanded positions as illustrated in, for example, FIG. 1. In addition, the catheter of the present invention can be used to perform "radial" mapping procedures, ablation procedures, and temperature measurement and control. That is, the outer circumferential edge 76, illustrated, for example, in FIG. 8, can be applied against an inner circumferential surface of a blood vessel.

Furthermore, being able to use the same catheter for both mapping and ablation procedures has the potential to reduce procedure time and reduce X-ray exposure.

The ability to expand braided conductive member 28 in an artery or vein against a tissue structure such as a freewall or ostium can provide good contact pressure for multiple electrodes and can provide an anatomical anchor for stability. Temperature sensors can be positioned definitively against the endocardium to provide good thermal conduction to the tissue. Lesions can be selectively produced at various sections around the circumference of braided conductive member 28 without having to reposition catheter 10. This can provide more accurate lesion placement within the artery or vein. Braided conductive member 28, in its radially expanded position as illustrated in particular in FIGS. 1 and 8 is advantageous because, in these embodiments, it does not block the blood vessel during a mapping or ablation procedure, but allows blood flow through the braided conductive member thus allowing for longer mapping and/or ablation times, which can potentially improve accuracy of mapping and efficacy of lesion creation.

Methods Of Use

Reference is now made to FIGS. 25-31, which related to methods of using the catheter 10 described above. The methods are directed to the treatment of a heart condition, e.g., atrial fibrillation, via the measurement and ablation of inter-atrial conductive pathways.

Figure 25A:
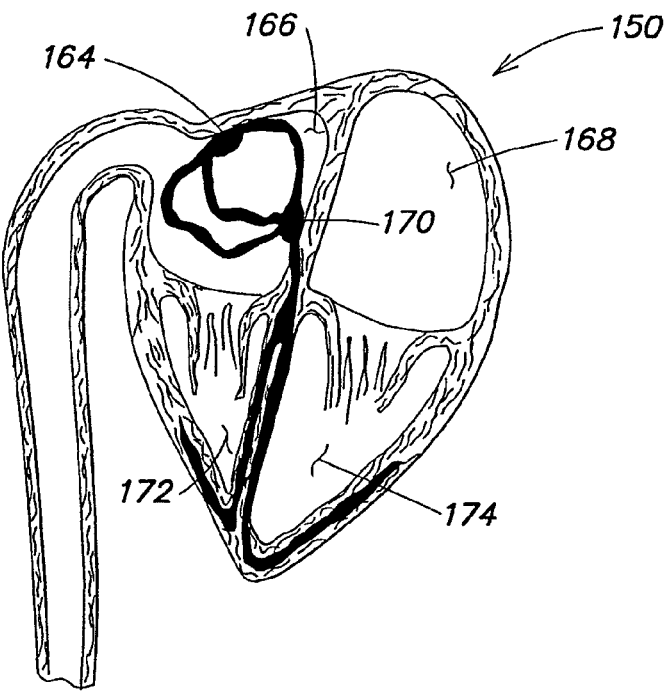

FIG. 25A illustrates a portion of the conduction system of the heart 150. The sinoatrial (SA) node 164, located at the top of the right atrium 166, is the natural "pacemaker" of the heart. The SA node 164 initiates the heartbeat by emitting an electrical signal that rapidly propagates throughout the left atrium 168 and the right atrium 166, and causes both atria to contract. The signal then travels to the atrioventricular (AV) node 170, located above the opening of the coronary sinus in the inter-atrial septum of the right atrium 166. The AV node propagates the signal to the muscle fibers of the right ventricle 172 and left ventricle 174, which then also contract. The normal sequence of electrical activation of the chambers of the heart is called sinus rhythm.

Abnormalities may exist in the heart's conduction rhythms. For example, atrial fibrillation is an abnormality of heart rhythm in which the atria of the heart no longer contract in an organized manner. In atrial fibrillation, sinus rhythm does not occur. Instead, electrical impulses travel randomly through the atria, leading to the activation of different parts of the atria at different times. The uncoordinated activation of the atria causes the walls of the atria quiver or "fibrillate." Atrial fibrillation may result in a number of detrimental conditions, including chest palpitations, stroke, and heart failure.

Figure 25B:
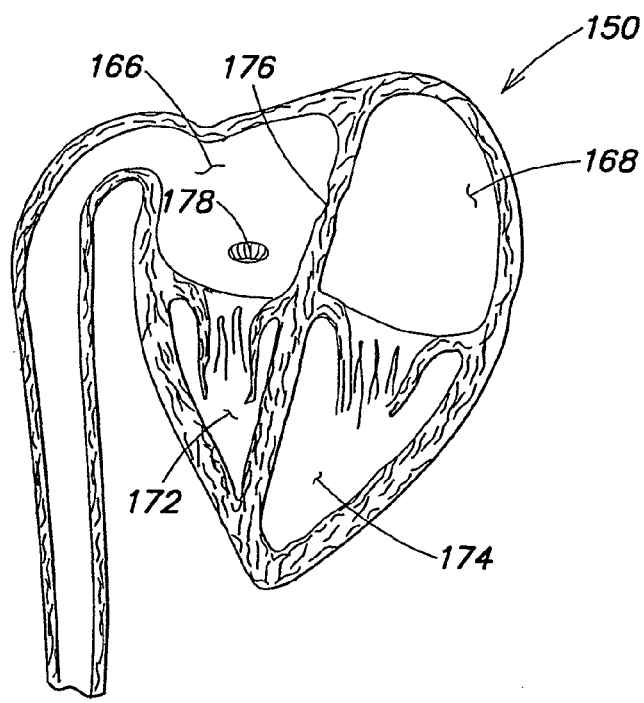

One treatment for atrial fibrillation is ablation, e.g., using RF energy, of the tissues and pathways that give rise to the errant signals. Ablation of the tissue alters the conductivity of the tissue. This may include suppressing, reducing, or eliminating the ability of the tissue to conduct or generate impulses. To detect foci that originate errant signals or pathways that conduct errant signals, electrophysiological mapping may be performed. Electrophysiology studies have revealed that the coronary sinus and fossa ovalis are potential pathways for the conduction of errant impulses between the atria. The coronary sinus is a blood vessel that carries deoxygenated blood from the cardiac muscle tissue into the right atrium. The fossa ovalis is an oval depression on the lower part of the inter-atrial septum of the right atrium, and corresponds to the location of the foramen ovale in the fetus. FIG. 25B illustrates the location of the fossa ovalis 176 and the opening of the coronary sinus 178 in the right atrium 166.

According to the present invention, a catheter having a braided conductive member, as described in connection with previous embodiments, may be used to ablate tissue at the fossa ovalis or coronary sinus to inhibit or reduce the conduction of electrical impulses in at least one direction between the atria of the heart. Thus, a partial or complete block of conduction may be formed. Further, the catheter may be used to measure signals or properties of the heart such as baseline electrical activity, conduction via ablated pathways, and lesion quality. One advantage of using a catheter according to the invention in the described method is that only a single catheter is necessary to (1) create a lesion at the coronary sinus and/or fossa ovalis, and (2) perform any desired electrical measurements, such as to determine the quality of the lesion or the degree of conductivity of the coronary sinus or fossa ovalis. This avoids the need for changing catheters, for example, between mapping and ablation procedures. It may also reduce the number of removal and reinsertion operations needed during an electrophysiology study and treatment procedure.

Figure 26A:
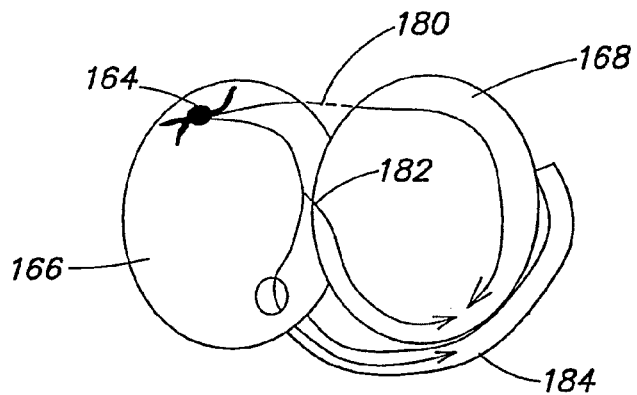
Figure 26B:
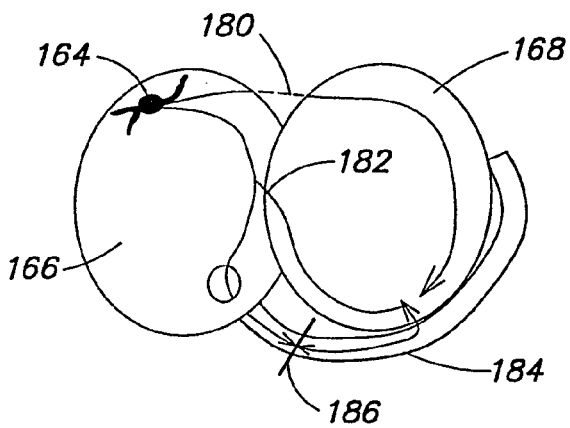
Figure 26C:
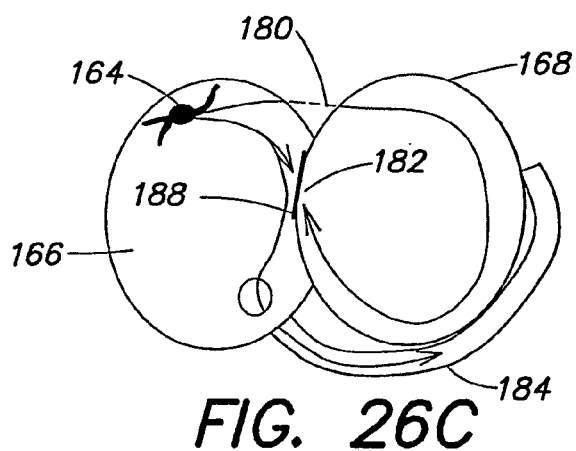

Reference is now made to FIGS. 26A-C, which illustrate examples of the conduction of electrical impulses through the atria before ablation (FIG. 26A), after ablation at the coronary sinus (FIG. 26B), and after ablation at the fossa ovalis (FIG. 26C). Three preferential pathways for the conduction of electrical signals are illustrated in FIG. 26A. These pathways are Bachmann's bundle 180, the fossa ovalis 182, and the coronary sinus 184.

Bachmann's bundle 180 is a specialized path for inter-atrial conduction that extends from the SA node 164 and is critical in propagating the signal initiated by the SA node to the left atrium 168 to stimulate contraction of the left atrium 168. While ablation of Bachmann's bundle 180 may be beneficial in treating atrial fibrillation, ablation of this area may impair the normal conduction system of the heart. In particular, ablation of Bachmann's bundle 180 may result in inadequate activation of the tissue on the atria, and a resultant inability of the atria to properly contract. Patients that undergo electrical disconnection in this region typically need artificial activation of the atria (e.g., using a pacemaker) to sustain a normal heartbeat. Thus, it may be advantageous to maintain the conduction pathway of Bachmann's bundle 180 to retain the heart's ability to contract, and alter the conductivity of one or more alternative preferential inter-atrial conductive pathways. Ablation of one or more alternative inter-atrial conductive pathways may reduce or eliminate the occurrence of atrial fibrillation in the patient. Two such pathways, the fossa ovalis 182 and coronary sinus 184, are discussed in connection with FIGS. 26B-C. However, it should be appreciated that other pathways may exist for the transmission of errant impulses, and the invention is not limited to application at the described locations. Further, though ablation at Bachmann's bundle 180 may have deleterious effects, there may be circumstances where such ablation may be beneficial and thus ablation of Bachmann's bundle 180 may be performed in accordance with the present invention.

FIG. 26B illustrates the conduction of electrical impulses through the atria after ablation of the coronary sinus 184 at a lesion location 186. While signals may travel from the right and left atria into the coronary sinus 184, conduction in at least one direction across lesion location 186 is reduced or eliminated. By ablating the coronary sinus pathway 184, the inter-atrial conduction of errant signals via the coronary sinus 184 may be reduced or eliminated, thereby reducing or eliminating atrial fibrillation. As shown, the conductive pathways of Bachmann's bundle 180 and the fossa ovalis 182 are maintained.

FIG. 26C illustrates the conduction of electrical impulses through the atria after ablation of the fossa ovalis 182 at a lesion location 188. Conduction across lesion location 186 is reduced or eliminated in at least one direction after ablation at the fossa ovalis 182. By ablating the fossa ovalis pathway 182, the inter-atrial conduction of errant signals, and hence atrial fibrillation, may be reduced or eliminated. As shown, the conductive pathways of Bachmann's bundle 180 and coronary sinus 184 are maintained.

To determine one or more pathways for ablation, a physician may measure heart signals during atrial fibrillation, which represents a baseline analysis. Baseline analysis may be performed, for example, using electrodes positioned such that the direction of propagation of signals can be determined at locations in the heart, including the atria and/or ventricles. The baseline information indicates which pathways, if any, conduct errant signals. Ablation may be performed at one or both of the coronary sinus 184 and fossa ovalis 182 in accordance with the present invention. For example, ablation at the coronary sinus 184 alone may be sufficient for treatment of atrial fibrillation in a particular patient. In addition to being used to determine an ablation site, baseline heart signal characteristics may be compared with post-ablation heart signal characteristics to provide an indication of success of ablation. In particular, the activation sequence of the heart tissue will change in a predictable manner after successful ablation of a pathway. According to one embodiment of the present invention, baseline analysis may be preformed using a catheter, as described herein, that may also be used for ablation.

As discussed above, after ablation of a pathway, it is desirable to confirm that the desired amount of conductive alteration of the pathway has been achieved. One way this can be achieved is by emitting an electrical signal on one side of the lesion and detecting a received electrical signal on the other side of the lesion. The degree to which the signal is propagated across the lesion indicates the conductive alteration of the pathway. However, during the ablation process it may be useful to obtain a preliminary indication of the conductive alteration of the pathway. The quality of the lesion formed during ablation correlates well with the degree of conductive alteration of the pathway, and may be easier to measure. Lesion quality may be determined by measuring electrical signals within the lesion itself to determine the strength of the electrical signals in the lesion and/or the impedance of the tissue in the lesion. In general, the higher the lesion quality, the higher the degree of conductive alteration of the pathway. According to one embodiment of the present invention, the degree of conductive alteration of a pathway and/or the quality of a lesion may be measured using a catheter, as described herein, that may also be used for ablation.

Figure 27A:
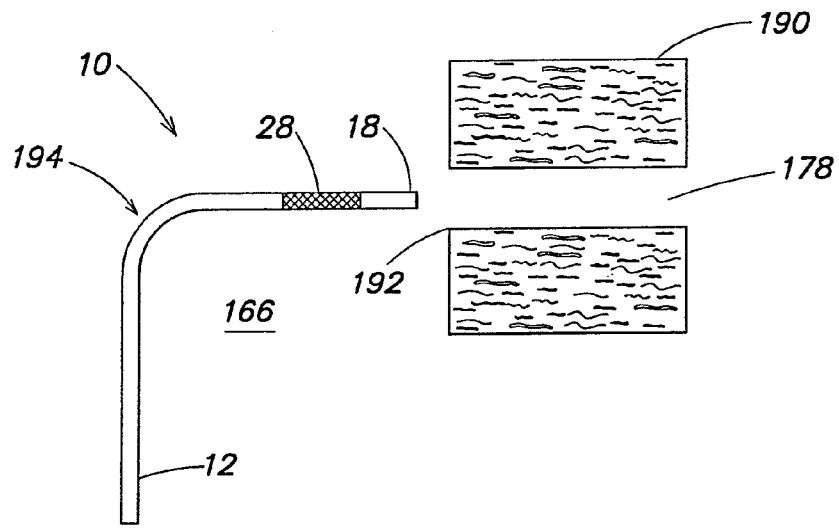
Figure 27B:
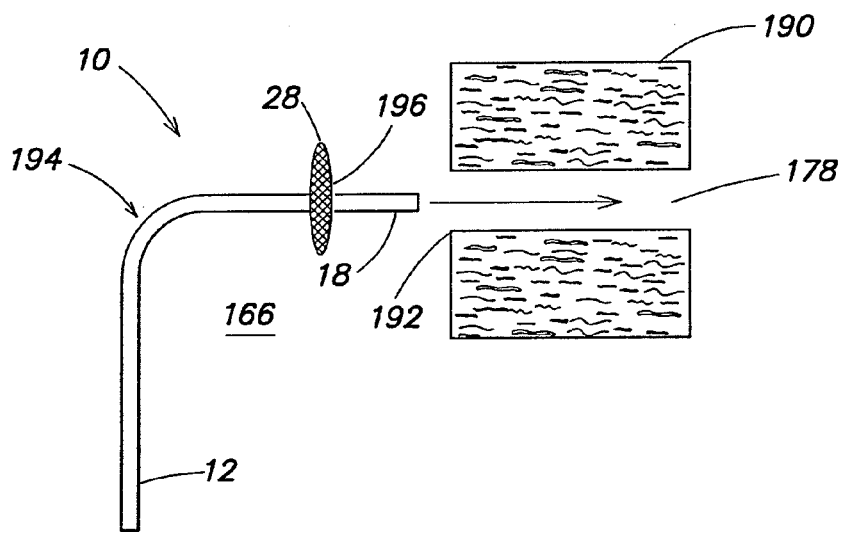
Figure 27C:
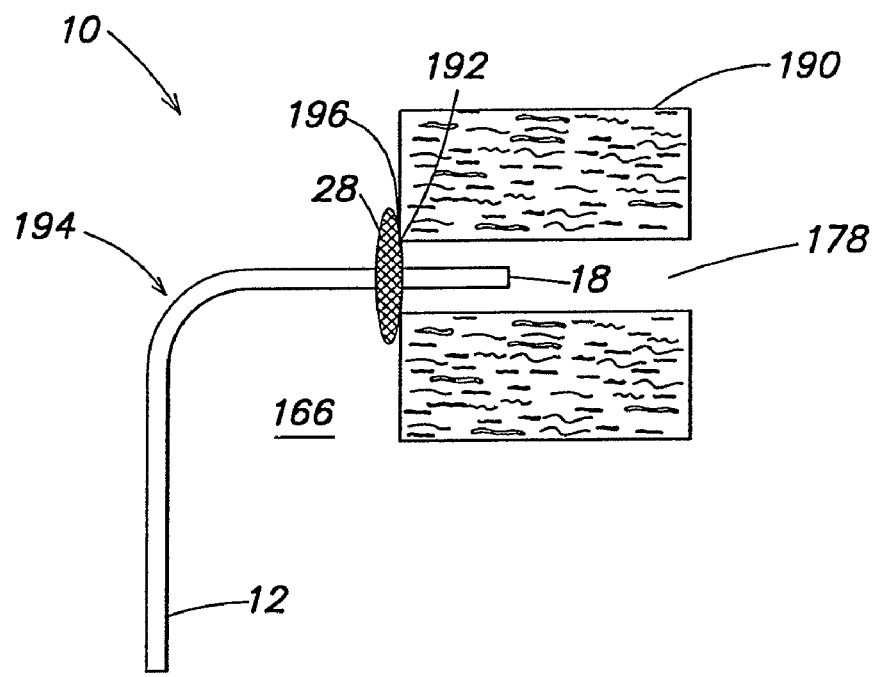

Having thus described several features of the catheter 10, various methods for using the catheter 10 will be described. Reference is now made to FIGS. 27A-C, which illustrate a method of using catheter 10 having a braided conductive member 28 to perform ablation and/or mapping at the ostium 192 of the coronary sinus 178 in the right atrium 166. Catheter 10 is first introduced into the right atrium 166 with the braided conductive member 28 in an undeployed position, as shown in FIG. 27A. A steerable portion 194 is shown on catheter 10, proximal to the braided conductive member 28. While the catheter 10 of FIGS. 27A-C is shown as having a steerable portion 194 located proximal to the braided conductive member 28, it is not necessary to performing the method of FIGS. 27A-C. Further, though steerable portion 194 is not shown in connection with other embodiments, it should be appreciated that any of the embodiments described herein may employ proximal steering, distal steering, or any combination.

As shown in FIG. 27B, the braided conductive member 28 is deployed in the right atrium 166. The braided conductive member 28 may be partially or fully deployed. Further, the deployed braided conductive member 28 may assume any number of shapes or configurations. For example, the braided conductive member 28 may have a non-circular edge in the deployed configuration, as shown in FIG. 15A, or may have an asymmetric shape in the deployed configuration, as shown in FIG. 15B. In another example, the braided conductive member 28 may be deformable, as shown in U.S. Pat. No. 6,315,778 which is hereby incorporated by reference. The catheter 10 may assume any number of alternate configurations. For example, the catheter 10 may not include distal tip portion 18, as shown in FIGS. 16A-16C. It should be appreciated that the variations described above may be incorporated in any of the embodiments described herein.

The distal tip portion 18 of catheter 10 is then maneuvered into the coronary sinus 178 until the braided conductive member 28 is near or in contact with cardiac tissue 190 at the ostium 192 of the coronary sinus 178, as shown in FIG. 27C. The distal tip potion 18 advantageously aids in positioning the braided conductive member 28 at the ostium 192 and in stabilizing the braided conductive member 28 at that location. The maneuverability of the catheter 10 proximal to the braided conductive member 28 also aids in the positioning of the braided conductive member 28. Once the braided conductive member 28 is positioned, ablative energy may then applied to the ostium 192 via the braided conductive member 28. Braided conductive member 28 may form a ring-shaped lesion around the opening of the coronary sinus 178, although the lesion need not be complete. A lesion of any shape that substantially or sufficiently inhibits the inter-atrial conduction via the coronary sinus 178 in at least one direction may successfully reduce or inhibit atrial fibrillation.

For this and other embodiments, it should be appreciated that the ablation may be tuned for a specific application by adjusting specified parameters. For example, power, temperature, duration of application, and number of RF applications may all be varied to achieve desired results, as is well known in the art.

The braided conductive member 28 of this embodiment may be specialized for ablation at the ostium 192 of the coronary sinus 178. For example, insulation may be selectively removed from the filaments of the braided conductive member 28 on the distal side 196 of braided conductive member 29. Temperature sensors may be incorporated in the braided conductive member 28, as described herein, and may be used to indicate the temperature of the tissue during ablation. In addition to serving an ablative function, the braided conductive member 28 may also be used to assess the quality of the lesion at the ostium 192 and/or the conductivity via the coronary sinus 178 before or after ablation.

Figure 28A:
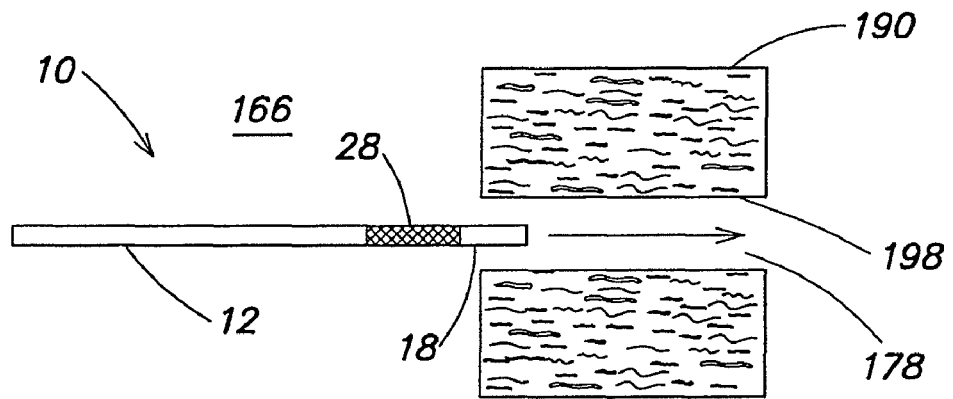
Figure 28B:
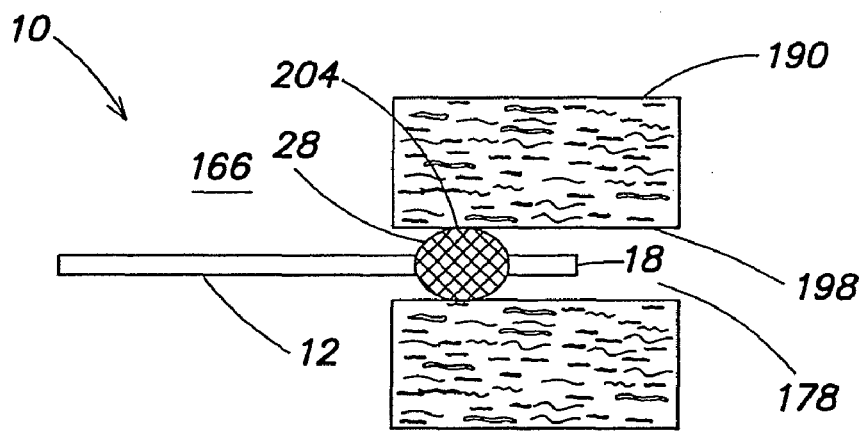

Reference is now made to FIGS. 28A-B, which illustrate a method of using a catheter 10 having a braided conductive member 28 to perform ablation and/or mapping at a location of the wall 198 of the coronary sinus 178. Catheter 10 is first introduced into the right atrium 166 with the braided conductive member 28 in an undeployed position. Next, the distal tip portion 18 and braided conductive member 28 of the catheter 10 are inserted into the coronary sinus 178, as shown in FIG. 28A.

When the braided conductive member 28 is aligned with the desired ablation location, the braided conductive member 28 is deployed in so that it is in contact with the wall 198 of the coronary sinus 178. Once the braided conductive member 28 is deployed, ablative energy may be applied to the wall 198 of the coronary sinus 178 via the braided conductive member 28, or electrical measurements may be performed using braided conductive member 28. In FIG. 28B, the braided conductive member 28 is partially deployed, and the braided conductive member 28 is in contact with a band-shaped region of the coronary sinus 178. However, the braided conductive member may be fully deployed, and may be in contact with a narrower ring-shaped region of the coronary sinus 178. The size of the braided conductive member may be chosen according to the shape of the region desired to be ablated, as well as other factors. Further, as discussed in connection with the embodiment of FIGS. 27A-C, the deployed braided conductive member 28 may assume any number of shapes or configurations.

The braided conductive member 28 of this embodiment may be specialized for ablation of the wall 198 of the coronary sinus 178. For example, insulation may be removed from the filaments of the braided conductive member 28 near the circumferential region 204 of the braided conductive member 28 that contacts the wall 198 of the coronary sinus 17. Temperature sensors may be incorporated into the braided conductive member 28, as discussed above. Further as discussed above, the braided conductive member 28 may be used to assess the quality of the lesion at the wall 198 of the coronary sinus 178 and/or the conductivity via the coronary sinus 178.

Figure 29A:
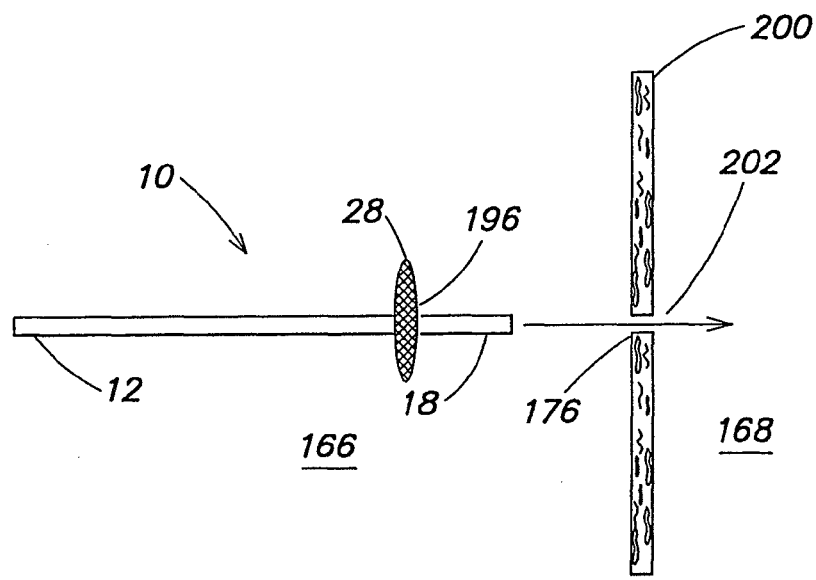
Figure 29B:
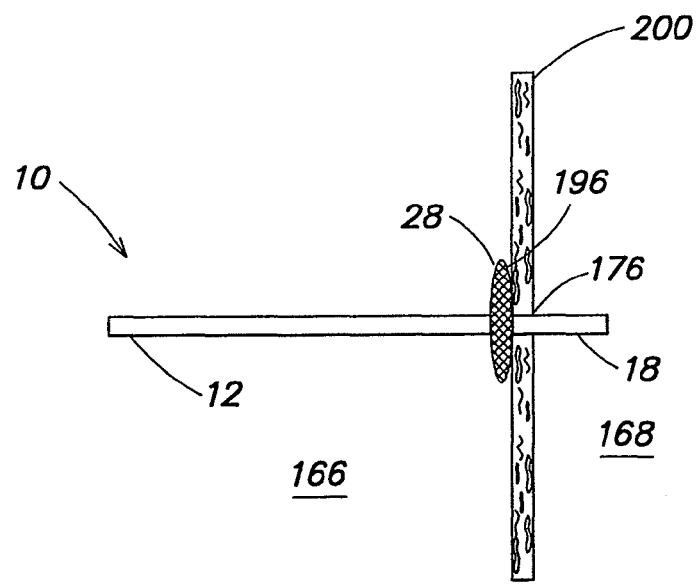

Reference is now made to FIGS. 29A-B, which illustrate a method of using a catheter 10 having a braided conductive member 28 to perform ablation and/or mapping at the fossa ovalis 176 in the right atrium 166. The fossa ovalis 176 is an area of the inter-atrial septum 200 having a decreased thickness relative to surrounding areas. Because the surface of the inter-atrial septum 200 at the location of the fossa ovalis 176 is smooth, it is difficult to form good contact between an electrode and the fossa ovalis 176. Loss of contact between the electrode and the fossa ovalis 176 during ablation can have serious negative effects, including accidental ablation of the nearby AV node. Thus, according to one embodiment of the invention, a puncture 202 may be made in the inter-atrial septum 200 at the fossa ovalis 176. The puncture may be formed, for example, using a needle-bearing catheter. The puncture 202 may be used to accommodate a distal tip portion 18 of the catheter 10, and thereby hinder movement of the catheter 10 during ablation or mapping.

Catheter 10 is introduced into the right atrium 166, where the braided conductive member 28 is deployed. The braided conductive member 28 may be partially or fully deployed and may have any of a number of configurations as described above. Next, as shown in FIG. 29A, the distal tip portion 18 of catheter 10 is passed from the right atrium 166 to the left atrium 168 through the inter-atrial septum 200. The catheter 10 is advanced in the direction of inter-atrial septum 200 until the distal side 196 of the braided conductive member 28 contacts the inter-atrial septum 200 of the right atrium 166 at the fossa ovalis 176.

The braided conductive member 28 of this embodiment may be specialized for ablation at the right atrium wall of the fossa ovalis 176. For example, as discussed in connection with the embodiment of FIGS. 27A-C, insulation may be selectively removed from the filaments of the braided conductive member 28 on the distal side 196 of braided conductive member 28. Temperature sensors may also be incorporated in the braided conductive member 28. The braided conductive member 28 may be used to assess the quality of the lesion at the fossa ovalis 176 and/or the conductivity via the fossa ovalis 176.

Figure 30A:
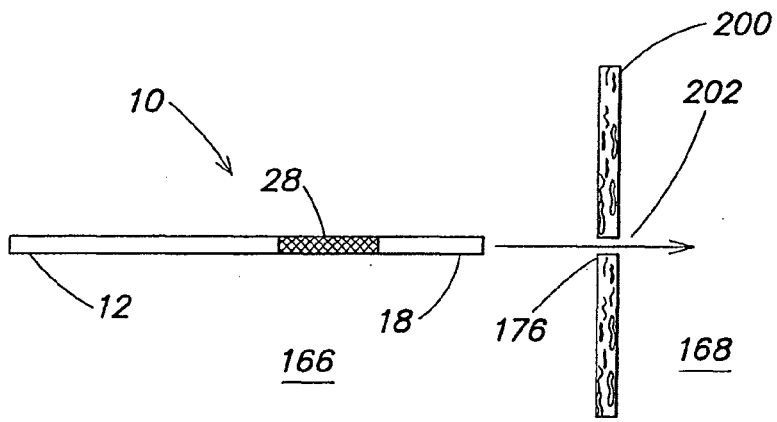
Figure 30B:
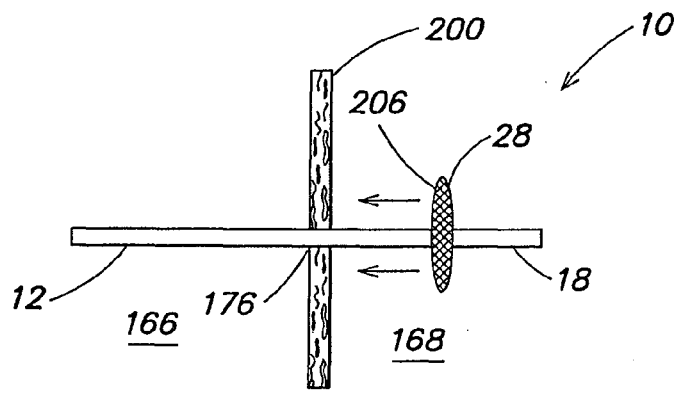
Figure 30C:
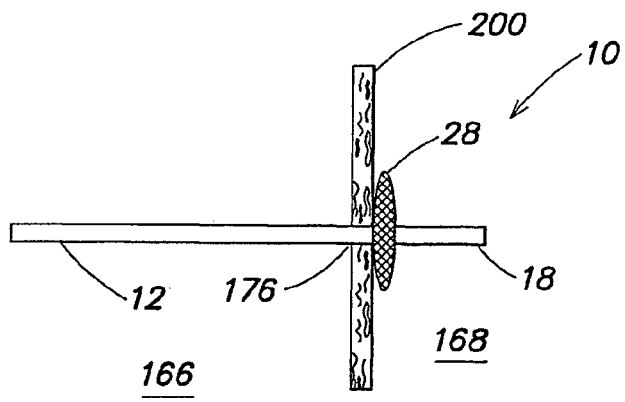

Reference is now made to FIGS. 30A-C, which illustrate a method of using a catheter 10 having a braided conductive member 28 to perform ablation and/or mapping at the fossa ovalis 176 in the left atrium 168. As discussed in connection with the embodiment of FIGS. 29A-B, the surface of the inter-atrial septum 200 at the location of the fossa ovalis 176 is smooth, and it is therefore difficult to form good contact between an electrode and the fossa ovalis 176. Thus, according to one embodiment of the invention, a puncture 202 may be made in the inter-atrial septum 200 at the fossa ovalis 176, through which a portion of catheter 10 may be passed. In the example of FIGS. 30A-C, a distal tip portion 18 and braided conductive member 28 of catheter 10 are passed through the puncture 202 into the left atrium.

Catheter 10 is introduced into the right atrium 166 with the braided conductive member 28 in an undeployed position. Next, as shown in FIG. 30A, the distal top portion 18 and braided conductive member 28 of catheter 10 are passed from the right atrium 166 to the left atrium 168 through the inter-atrial septum 200. Once in the left atrium 168, the braided conductive member 28 is deployed. The braided conductive member 28 may be partially or fully deployed and may have any of a number of configurations as described above. Further, temperature sensors may be incorporated in the braided conductive member 28.

As shown in FIG. 30B, once the braided conductive member 28 is deployed, the catheter 10 is pulled back towards the right atrium 166. The catheter 10 is retracted in the direction of inter-atrial septum 200 until the proximal side 206 of the braided conductive member 28 contacts the inter-atrial septum 200 of the left atrium 168 at the fossa ovalis 176. When the braided conductive member 28 is near or in contact with the inter-atrial septum 200, ablative energy may be applied to the fossa ovalis 176 via the braided conductive member.

The braided conductive member 28 of this embodiment may be specialized for ablation at the right atrium wall of the fossa ovalis 176. For example, as discussed in connection with the embodiment of FIGS. 27A-C, insulation may be selectively removed from the filaments of the braided conductive member 28 on the distal side 196 of braided conductive member 29. The braided conductive member 28 may also be used to assess the quality of the lesion at the fossa ovalis 176 and/or the conductivity via the fossa ovalis 176.

Figure 31A:
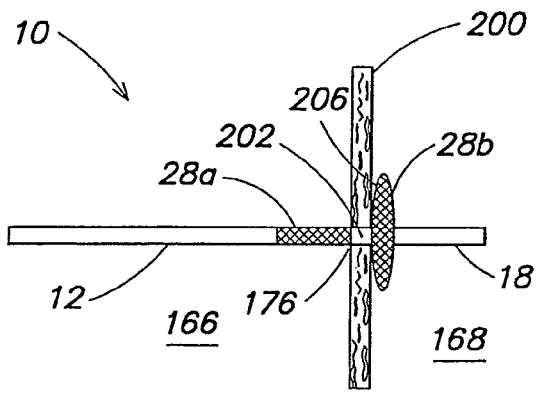
Figure 31B:
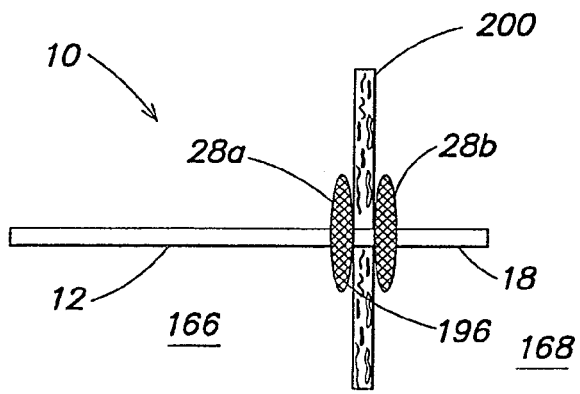

Reference is now made to FIGS. 31A-B, which illustrate a method of using a catheter 10 having a proximal braided conductive member 28a and a distal braided conductive member 28b to perform ablation and/or mapping at the fossa ovalis 176 in the right atrium 166 and left atrium 168, respectively. Both braided conductive members 28a-28b are undeployed when the catheter 10 is introduced into the right atrium 166. As described in connection with the embodiment of FIGS. 30A-C, the distal tip portion 18 and distal braided conductive member 28b of catheter 10 may be passed through the puncture 202 in inter-atrial septum 200 into the left atrium 168. The distal braided conductive member 28b is then deployed is the left atrium 168. The distal braided conductive member 28b may be partially or fully deployed and may have any of a number of configurations as described above. Further, temperature sensors may be incorporated in the distal braided conductive member 28b. Once the distal braided conductive member 28b is deployed, the catheter 10 is pulled back towards the right atrium 166. The catheter 10 is retracted in the direction of inter-atrial septum 200 until the proximal side 206 of the distal braided conductive member 28b contacts the inter-atrial septum 200 of the left atrium 168 at the fossa ovalis 176, as shown in FIG. 31A.

Next, the proximal braided conductive member 28a is deployed in the right atrium 166. Similarly, the proximal braided conductive member 28a may be partially or fully deployed and may have any of a number of configurations as described above. The distal braided conductive member 28b may be deployed by compression in a distal-to-proximal direction, while the proximal braided conductive member 28a may be deployed by compression in a proximal-to-distal direction. Thus, when proximal braided conductive member 28a is deployed, it contacts the inter-atrial septum 200 of the right atrium 166 at the fossa ovalis 176, as shown in FIG. 31B.

When the braided conductive members 28a-28b are near or in contact with the inter-atrial septum 200, ablative energy may be applied from both atria to the fossa ovalis 176 via the braided conductive members 28a-28b. The proximal and distal braided conductive members 28a-28b may have insulation that is selectively removed from the filaments on the distal side 196 and proximal side 206 of the proximal and distal braided conductive members 28a-28b, respectively. The braided conductive members 28a-28b, either alone or in combination, may also be used to assess the quality of the lesion at the fossa ovalis 176 and/or the conductivity via the fossa ovalis 176.

For any of the above described methods, it should be appreciated that appropriate imaging guidance (direct visual assessment, camera, fluoroscopy, echocardiographic, magnetic resonance, etc.) may be used to assist in positioning of the braided conductive member 28 relative to a target ablation or measurement site.

Shaft electrodes

Figure 32:
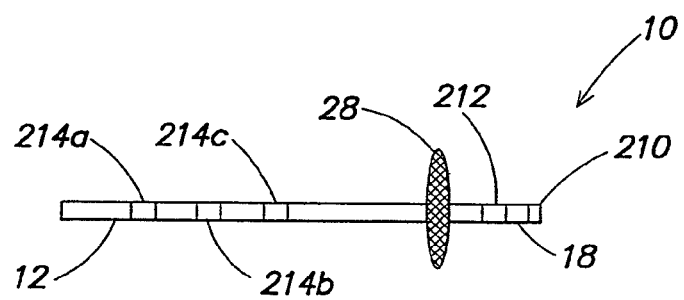
FIG. 32 illustrates the use of electrodes on the shaft of the catheter.

Reference is now made to FIG. 32, which illustrates a catheter 10 having a braided conductive member 28 and electrodes disposed on the shaft 12 of the catheter. The catheter 10 of FIG. 32 includes two electrodes on the distal tip portion 18 of the catheter 10, an electrode 210 on the distal tip and an electrode 212 proximal to the electrode 210. Further, the catheter 10 includes electrodes 214a-c, proximal to the braided conductive member 28. Although a particular electrode configuration is illustrated, it should be appreciated that the invention is not limited to this configuration, and that many alternative types and placements of electrodes are possible. Further, though electrodes are not illustrated on the shaft 12 of the catheter 10 of other embodiments herein, any of the described embodiments may or may not include such electrodes.

The electrodes on the shaft 12 of the catheter 10 may perform mapping functions, such as performing a baseline analysis of the electrical conductivity of the heart or assessing the conductivity of an electrical pathway. For example, electrodes 214a-c may be used to select a pathway for ablation. When the catheter 10 is in the right atrium for example, the shaft 12 may be positioned so that the electrodes 214a-c contact the right atrium at various points. Based on the electrical signal received at each, and the time of receipt of the signal by each electrode, the direction of propagation of the electrical impulses in the right atrium can be measured. This data may be used to determine the conductive pathways of the heart and, thereby, locations for ablation.

With successful coronary sinus ablation, the activation sequence of the near field coronary sinus musculature will change from an "ostium to distal" sequence (before ablation) to a "distal to ostium" sequence (after ablation). The coronary sinus will be activated via distal left atrium to coronary sinus connections. With successful fossa ovalis ablation after successful coronary sinus ablation, the left atrium activation sequence will change from a "septal to lateral" sequence (before ablation) to a "lateral to septal" sequence (after ablation) since the left atrial activation is still intact via Bachmann's Bundle and thus proceeds from cranial to caudal. The electrodes 214a-c may be used as described above to determine the activation sequence of the heart after ablation of the coronary sinus and/or fossa ovalis, and thereby determine the degree of conductive alteration of these pathways.

A pair of electrodes, e.g., electrodes 214c and 212, may be used to measure the conductivity of an electrical pathway before or after ablation. For example, electrode 212 may be designated as a pacing electrode and electrode 214c may be designated as a measurement electrode. The electrodes may be placed in contact with the cardiac tissue in a conductive pathway. The pacing electrode emits a signal for detection by the measurement electrode. Before ablation of a pathway, the heart tissue will be healthy and a strong signal will be received by the measurement electrode based on the emitted signal. However, if a pathway has been successfully conductively altered due to ablation, a signal emitted by the pacing electrode will be received very weakly or not at all by the measurement electrode. Thus, electrodes on the shaft 12 of the catheter 10 may be used to measure the conductivity of an ablated pathway.

A distal tip electrode 210 is also shown which may perform any number of functions. For example, the distal tip electrode 210 may be used as a unipolar electrode to detect an electrocardiogram at a location of the heart tissue or may be used as a reference electrode.

Experimental Data

Figure 33:
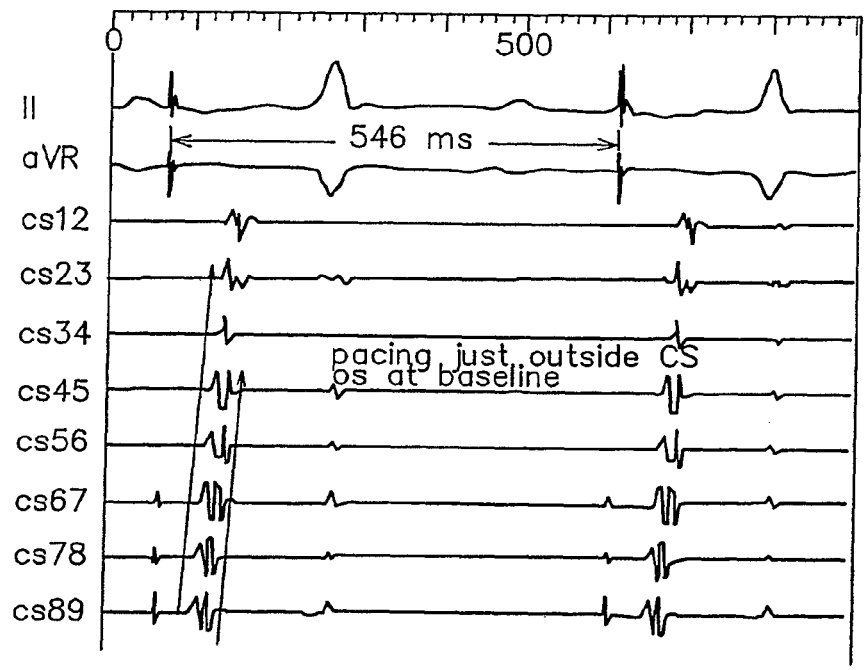
FIGS. 33-34 illustrate the coronary sinus activation sequence before and after ablation.
Figure 34:
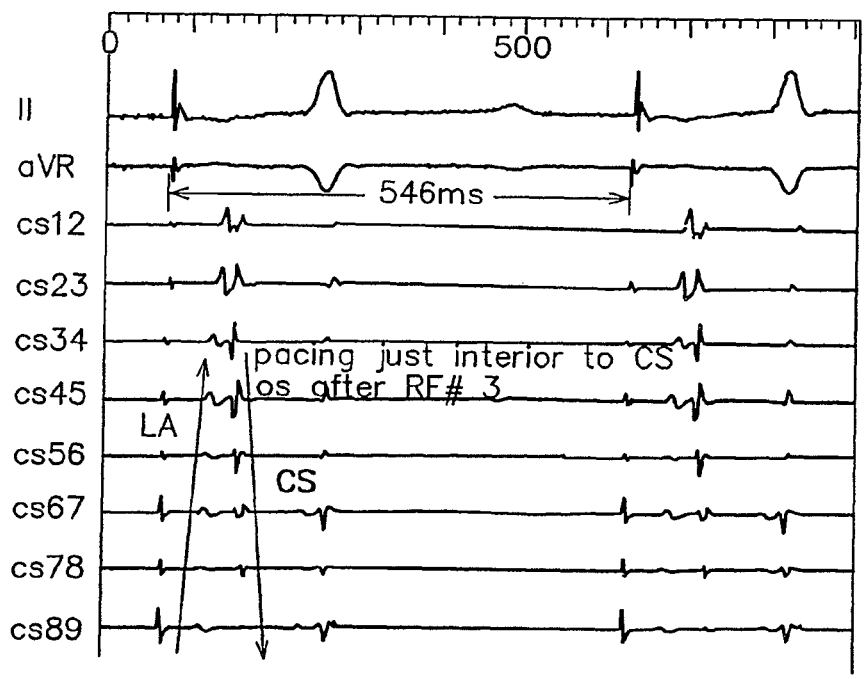

Catheter ablation of an inter-atrial conduction path for treatment of atrial fibrillation was investigated in a dog study. Under fluoroscopic guidance and ICE (Acuson), a multipolar electrode catheter was placed in the CS of dogs. The activation sequence was assessed during low right atrial (LRA) pacing. The CS catheter was then replaced with a mesh type electrode. RF energy was delivered just outside and just inside the CS os. After each ablation the CS mapping catheter was repositioned and activation sequence reevaluated. Pre and post-ablation recordings were also performed with the mesh type. CS access was achieved in 3 of 4 dogs. CS activation sequence during LRA pacing was proximal to distal (CS 8,9 to CS 1,2) in all animals (see FIG. 33). In addition, far field (low frequency) left atrial potentials were seen. After RF ablation the CS activation sequence was distal to proximal, consistent with conduction block in the CS (see FIG. 34). Macroscopic lesion evaluation showed circumferential lesions just inside the CS os.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting. The invention is limited only as defined in the following claims and the equivalents thereto.

The invention claimed is:

1. A method for treating a condition of the heart, comprising acts of:
   introducing a catheter into the heart, the catheter having a braided conductive member comprising a plurality of partially insulated filaments at a distal end thereof, wherein the braided conductive member comprises an ablative ring comprising uninsulated portions of filaments having a generally ring-shaped configuration;
   expanding the braided conductive member into a deployed configuration;
   contacting a selected location of the heart with the braided conductive member;
   forming a lesion on tissue at the selected location of the heart by energizing a plurality of filaments of the braided conductive member; and
   measuring the quality of the lesion using at least one filament of the braided conductive member.

2. The method of claim 1, wherein the act of forming a lesion on tissue at a selected location of the heart with the braided conductive member and the act of measuring the quality of the lesion with the braided conductive member are performed concurrently.

3. The method of claim 1, wherein the act of measuring the quality of the lesion with the braided conductive member includes measuring the impedance of the tissue at the selected location.

4. The method of claim 1, wherein the act of measuring the quality of the lesion with the braided conductive member includes measuring an amplitude of an electrical signal at the selected location.

5. The method of claim 1, wherein the ablative ring comprises a first uninsulated portion in contact with a second uninsulated portion adjacent to the first uninsulated portion.

6. The method of claim 1, wherein the ablative ring is distally-facing.

7. A method of operating a heart catheter having a braided conductive member comprising a plurality of partially insulated filaments, the braided conductive member comprising a plurality of ablation filaments for applying ablative energy to a surface of a heart, the plurality of ablation filaments comprising a first ablation filament having a first uninsulated portion and a second ablation filament having a second uninsulated portion in contact with the first portion when the braided conductive member is in a deployed configuration, and one or more mapping filaments for measuring an electrical signal at a surface of the heart, the method comprising expanding the braided conductive member into the deployed configuration, contacting a selected location of the heart with the braided conductive member, and activating the plurality of ablation filaments and the one or more mapping filaments concurrently.

8. The method of claim 7, wherein the heart catheter further includes means for steering the heart catheter.

9. The method of claim 8, wherein the means for steering the heart catheter includes means for manipulating a portion of the heart catheter to form a curve that is proximal to the braided conductive member.

10. The method of claim 7, wherein the braided conductive member comprises an ablative ring comprising uninsulated portions of filaments having a generally ring-shaped configuration, wherein the uninsulated portions comprise the first and second uninsulated portions.

11. The method of claim 10, wherein the ablative ring is distally-facing.

12. A method for treating a condition of a heart, comprising an act of:
   using a catheter having an expandable braided conductive member comprising a distally-facing ablative ring comprising uninsulated portions of filaments having a generally ring-shaped configuration to create a lesion at a wall of the right atrium at the fossa ovalis and/or a wall of the left atrium at the fossa ovalis, wherein the lesion is formed by the distally-facing ablative ring.

13. The method of claim 12, wherein the act of using the catheter further comprises using the distally-facing ablative ring to create a lesion at a wall of the coronary sinus.

14. The method of claim 13, further including an act of assessing the conductive alteration of the coronary sinus.

15. The method of claim 12, wherein the act of using the catheter further comprises using the distally-facing ablative ring to create a lesion at a wall of the right atrium at an opening of the coronary sinus.

16. The method of claim 15, further including an act of assessing the conductive alteration of the coronary sinus.

17. The method of claim 12, wherein the act of using the catheter further comprises using the distally-facing ablative ring to create a lesion at a wall of the right atrium at the fossa ovalis.

18. The method of claim 12, wherein the act of using the catheter further comprises using the distally-facing ablative ring to create a lesion at a wall of the left atrium at the fossa ovalis.

19. The method of claim 12, further including an act of reducing electrical conduction between the right atrium and left atrium of the heart.

20. The method of claim 19, further including an act of using the catheter to measure the electrical conduction between the right atrium and left atrium of the heart.

21. The method of claim 12, wherein the act of using the catheter comprises applying RF energy.

22. The method of claim 12, further including an act of using the catheter to measure a quality of the lesion.

23. A method for treating atrial fibrillation in a heart, comprising acts of:
   introducing a catheter into the heart, the catheter having a braided conductive member comprising a plurality of partially insulated filaments at a distal end thereof, wherein the braided conductive member comprises an ablative ring comprising uninsulated portions of filaments having a generally ring-shaped configuration;
   expanding the braided conductive member into a deployed configuration;
   contacting a selected location of the heart with the braided conductive member; and
   using the braided conductive member to ablate a region of the heart that serves as an electrical pathway between that left atrium and the right atrium of the heart to alter the conductivity of the electrical pathway.

24. The method of claim 23, wherein the act of using the catheter includes using the braided conductive member to ablate the coronary sinus.

25. The method of claim 24, wherein the act of using the catheter includes using the braided conductive member to reduce an electrical conductivity of the coronary sinus.

26. The method of claim 23, wherein the act of using the catheter includes using the braided conductive member to ablate the fossa ovalis.

27. The method of claim 26, wherein the act of using the catheter includes using the braided conductive member to reduce an electrical conductivity of the fossa ovalis.

28. The method of claim 23, wherein the ablative ring comprises a first uninsulated portion in contact with a second uninsulated portion adjacent to the first uninsulated portion.

29. The method of claim 23, wherein the ablative ring is distally-facing.

* * * * *